US010653535B2

(12) United States Patent
McCormack et al.

(10) Patent No.: US 10,653,535 B2
(45) Date of Patent: May 19, 2020

(54) APPARATUS AND METHOD FOR BONE SCREW DEPLOYMENT

(71) Applicant: Providence Medical Technology, Inc., Lafayette, CA (US)

(72) Inventors: Bruce M. McCormack, San Francisco, CA (US); Jeffrey D. Smith, Clayton, CA (US); Edward Liou, Pleasanton, CA (US); David Michael Schummers, San Francisco, CA (US)

(73) Assignee: Providence Medical Technology, Inc., Pleasanton, CA (US)

( * ) Notice: Subject to any disclaimer, the term of this patent is extended or adjusted under 35 U.S.C. 154(b) by 923 days.

(21) Appl. No.: 14/646,764

(22) PCT Filed: Dec. 6, 2013

(86) PCT No.: PCT/US2013/073744
§ 371 (c)(1),
(2) Date: May 22, 2015

(87) PCT Pub. No.: WO2014/089535
PCT Pub. Date: Jun. 12, 2014

(65) Prior Publication Data
US 2015/0297357 A1 Oct. 22, 2015

Related U.S. Application Data

(60) Provisional application No. 61/734,832, filed on Dec. 7, 2012, provisional application No. 61/766,186, filed on Feb. 19, 2013.

(51) Int. Cl.
*A61F 2/46* (2006.01)
*A61B 17/70* (2006.01)
(Continued)

(52) U.S. Cl.
CPC ........ *A61F 2/4611* (2013.01); *A61B 17/1604* (2013.01); *A61B 17/1671* (2013.01);
(Continued)

(58) Field of Classification Search
CPC ............... A61F 2/4611; A61B 17/1717; A61B 17/7082
(Continued)

(56) References Cited

U.S. PATENT DOCUMENTS 4,604,995 A 8/1986 Stephens et al.
5,584,832 A 12/1996 Schlapfer et al.
(Continued)

FOREIGN PATENT DOCUMENTS

FR 2941365 A1 7/2010
WO 9641582 A1 12/1996
(Continued)

OTHER PUBLICATIONS

Supplementary European Search Report dated Aug. 19, 2016 in connection with European Patent Application No. 13861379.9, 7 pages.
(Continued)

*Primary Examiner* — Si Ming Ku
(74) *Attorney, Agent, or Firm* — Dorsey & Whitney LLP

(57) ABSTRACT

Implementations described and claimed herein provide a bone anchor deployment device. In one implementation, the bone anchor deployment device includes a flexible shaft adapted to bend along a deployment trajectory. A socket at the distal end of the flexible shaft is adapted to retain a bone anchor in a non-coaxial position. The bone anchor deployment device further includes a guide shaft having a lumen and a distal tip and an elongated tube extending through at least a portion of the guide shaft lumen and protruding from the distal tip of the guide shaft. A guide passage extends through a lumen of the elongated tube, and a channel is
(Continued)

formed from a surface at a distal end of the guide passage. The channel is oriented at an angle relative to the guide passage and is adapted to cause the flexible shaft to bend.

20 Claims, 30 Drawing Sheets

(51) Int. Cl.
*A61B 17/17* (2006.01)
*A61B 17/16* (2006.01)
*A61B 17/80* (2006.01)
*A61F 2/44* (2006.01)
*A61B 17/86* (2006.01)
*A61F 2/30* (2006.01)
*A61B 17/88* (2006.01)

(52) U.S. Cl.
CPC ...... *A61B 17/1757* (2013.01); *A61B 17/7064* (2013.01); *A61B 17/7074* (2013.01); *A61B 17/7076* (2013.01); *A61B 17/7082* (2013.01); *A61B 17/8004* (2013.01); *A61B 17/86* (2013.01); *A61B 17/8635* (2013.01); *A61F 2/4455* (2013.01); *A61B 17/8805* (2013.01); *A61F 2002/30772* (2013.01); *A61F 2002/30774* (2013.01); *A61F 2002/30784* (2013.01); *A61F 2002/30785* (2013.01); *A61F 2002/30904* (2013.01); *A61F 2002/4687* (2013.01)

(58) Field of Classification Search
USPC .............................................. 606/104, 86 A
See application file for complete search history.

(56) References Cited

U.S. PATENT DOCUMENTS

| | | | |
|---|---|---|---|
| 5,941,885 A | 8/1999 | Jackson | |
| 5,971,987 A | 10/1999 | Huxel et al. | |
| 6,068,642 A | 5/2000 | Johnson et al. | |
| 6,565,605 B2 | 5/2003 | Fallin et al. | |
| 6,974,478 B2 | 12/2005 | Reiley et al. | |
| 7,090,698 B2 | 8/2006 | Fallin et al. | |
| 7,261,739 B2 | 8/2007 | Ralph et al. | |
| 7,491,240 B1 | 2/2009 | Carver et al. | |
| 7,662,157 B2* | 2/2010 | Ahmad | A61B 17/8875 606/104 |
| 7,682,393 B2 | 3/2010 | Trieu et al. | |
| 8,313,528 B1 | 11/2012 | Wensel | |
| 8,366,748 B2 | 2/2013 | Kleiner | |
| 8,382,839 B1 | 2/2013 | Wensel | |
| 8,523,945 B1 | 9/2013 | Wensel | |
| 8,551,175 B1 | 10/2013 | Wensel | |
| 8,747,412 B2 | 6/2014 | Bae et al. | |
| 8,753,377 B2 | 6/2014 | Liou et al. | |
| 8,834,472 B2 | 9/2014 | Liou et al. | |
| 8,870,882 B2 | 10/2014 | Kleiner | |
| 9,072,563 B2 | 7/2015 | Luby et al. | |
| 9,186,193 B2 | 11/2015 | Kleiner et al. | |
| 9,358,127 B2 | 6/2016 | Duffield et al. | |
| 9,427,264 B2 | 8/2016 | Kleiner et al. | |
| 9,717,403 B2 | 8/2017 | Kleiner et al. | |
| 9,730,805 B1 | 8/2017 | Wensel et al. | |
| 2005/0149192 A1 | 7/2005 | Zucherman et al. | |
| 2005/0234455 A1 | 10/2005 | Binder et al. | |
| 2006/0036259 A1 | 2/2006 | Carl et al. | |
| 2006/0039772 A1 | 2/2006 | Matthys-mark | |
| 2006/0085002 A1 | 4/2006 | Trieu et al. | |
| 2007/0050031 A1 | 3/2007 | Khosrowshahi | |
| 2007/0250167 A1 | 10/2007 | Bray et al. | |
| 2008/0033440 A1 | 2/2008 | Moskowitz et al. | |
| 2008/0045970 A1 | 2/2008 | Saidha et al. | |
| 2008/0154377 A1 | 6/2008 | Voellmicke | |
| 2009/0222092 A1 | 9/2009 | Davis et al. | |
| 2010/0049259 A1* | 2/2010 | Lambrecht | A61F 2/442 606/86 R |
| 2010/0076500 A1 | 3/2010 | Bray et al. | |
| 2010/0114105 A1 | 5/2010 | Butters et al. | |
| 2010/0191241 A1 | 7/2010 | McCormack et al. | |
| 2010/0211104 A1 | 8/2010 | Moumene et al. | |
| 2011/0077686 A1 | 3/2011 | Mishra et al. | |
| 2011/0230971 A1 | 9/2011 | Donner et al. | |
| 2011/0295327 A1 | 12/2011 | Moskowitz et al. | |
| 2012/0078373 A1 | 3/2012 | Gamache et al. | |
| 2012/0116466 A1 | 5/2012 | Dinville et al. | |
| 2012/0150301 A1 | 6/2012 | Gamache et al. | |
| 2012/0203290 A1 | 8/2012 | Warren et al. | |
| 2012/0226358 A1 | 9/2012 | Kleiner | |
| 2012/0265259 A1 | 10/2012 | LaPosta et al. | |
| 2013/0023889 A1 | 1/2013 | Blain et al. | |
| 2013/0103095 A1 | 4/2013 | Brumfield et al. | |
| 2013/0226300 A1 | 8/2013 | Chataigner et al. | |
| 2014/0012380 A1 | 1/2014 | Laurence et al. | |
| 2014/0074241 A1 | 3/2014 | McConnell et al. | |
| 2014/0276891 A1 | 9/2014 | Defalco et al. | |
| 2014/0277472 A1 | 9/2014 | Gray et al. | |
| 2015/0209089 A1 | 7/2015 | Bernard et al. | |
| 2015/0297357 A1 | 10/2015 | McCormack et al. | |
| 2015/0305887 A1 | 10/2015 | Hickey et al. | |
| 2015/0342648 A1 | 12/2015 | Mccormack et al. | |
| 2016/0100951 A1 | 4/2016 | Suddaby et al. | |
| 2016/0250035 A1 | 9/2016 | De Villiers et al. | |
| 2016/0331418 A1 | 11/2016 | Liou et al. | |
| 2016/0331553 A1 | 11/2016 | Liou et al. | |
| 2017/0027713 A1 | 2/2017 | Kleiner | |
| 2017/0172639 A1 | 6/2017 | DeFalco et al. | |
| 2018/0303631 A1 | 10/2018 | Phan et al. | |

FOREIGN PATENT DOCUMENTS

| | | |
|---|---|---|
| WO | 0053126 A1 | 9/2000 |
| WO | 0234120 A2 | 5/2002 |
| WO | 2009033100 A1 | 3/2009 |
| WO | 2014089535 A1 | 6/2014 |
| WO | 2016049784 A1 | 4/2016 |

OTHER PUBLICATIONS

International Search Report and Written Opinion dated Mar. 31, 2014 in connection with International Application No. PCT/US2013/073744, 9 pages.

European Examination Report for European Patent Application No. 13861379.9, dated Nov. 29, 2016 (7 pages).

European Search Opinion for European Patent Application No. 13861379.9, dated Feb. 20, 2017 (6 pages).

Stein et al., "Percutaneous Facet Joint Fusion: Preliminary Experience," Journal of Vascular and Interventional Radiology, Jan.-Feb. 1993, pp. 69-74, vol. 4, No. 1.

Examination report dated Sep. 28, 2018 in connection with European patent application No. 13861379.9, 4 pages, dated Sep. 28, 2018.

* cited by examiner

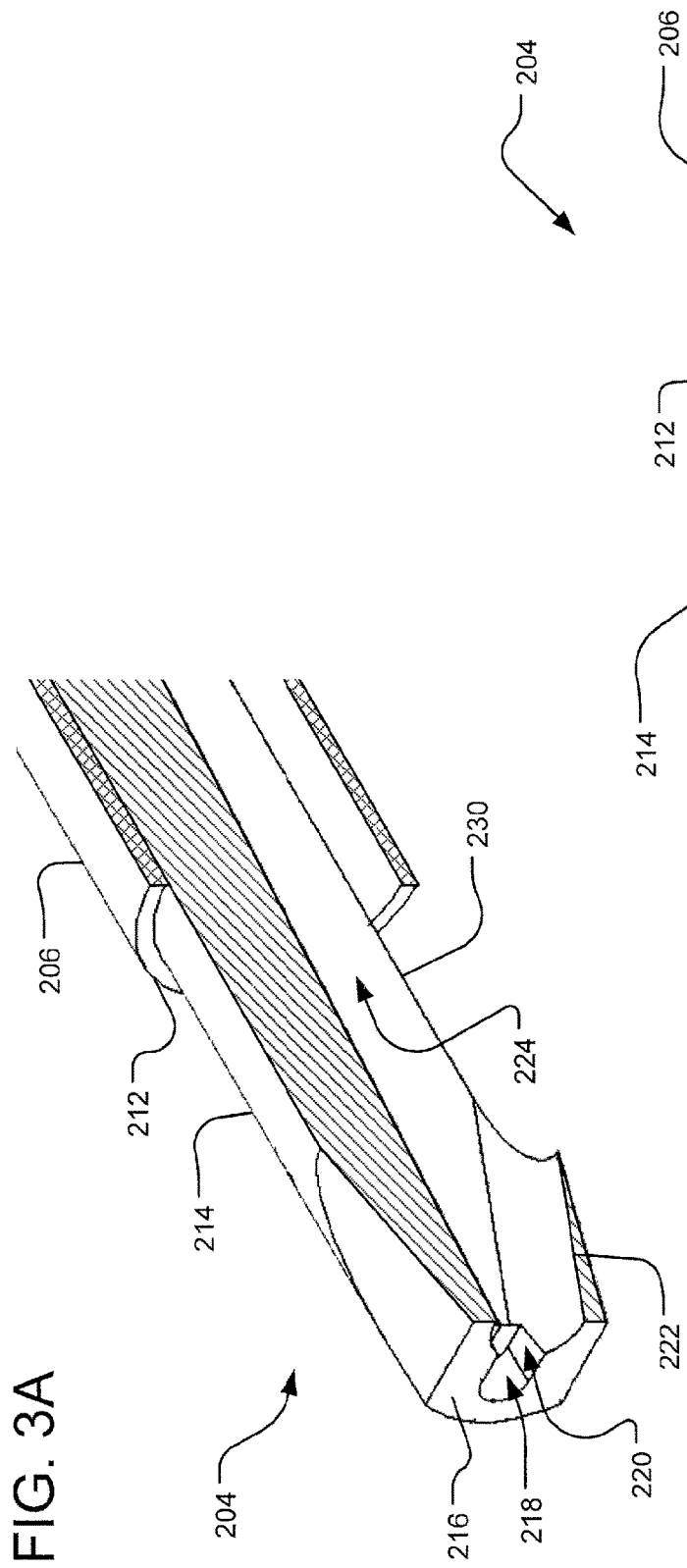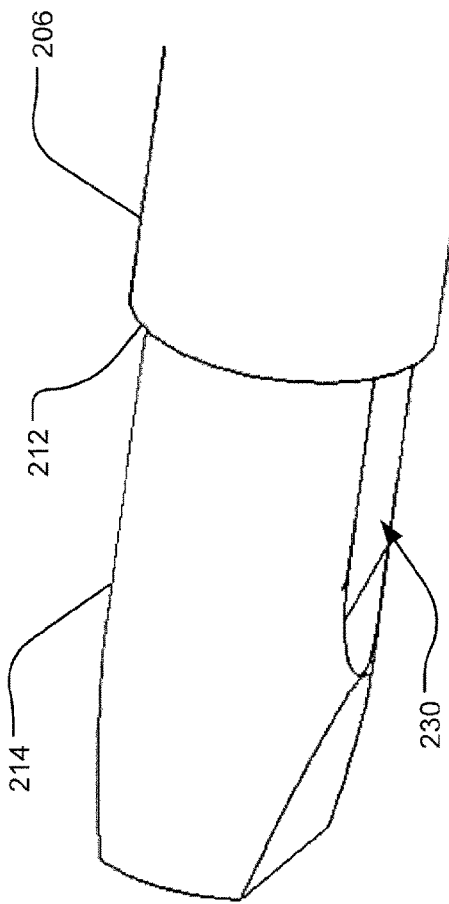

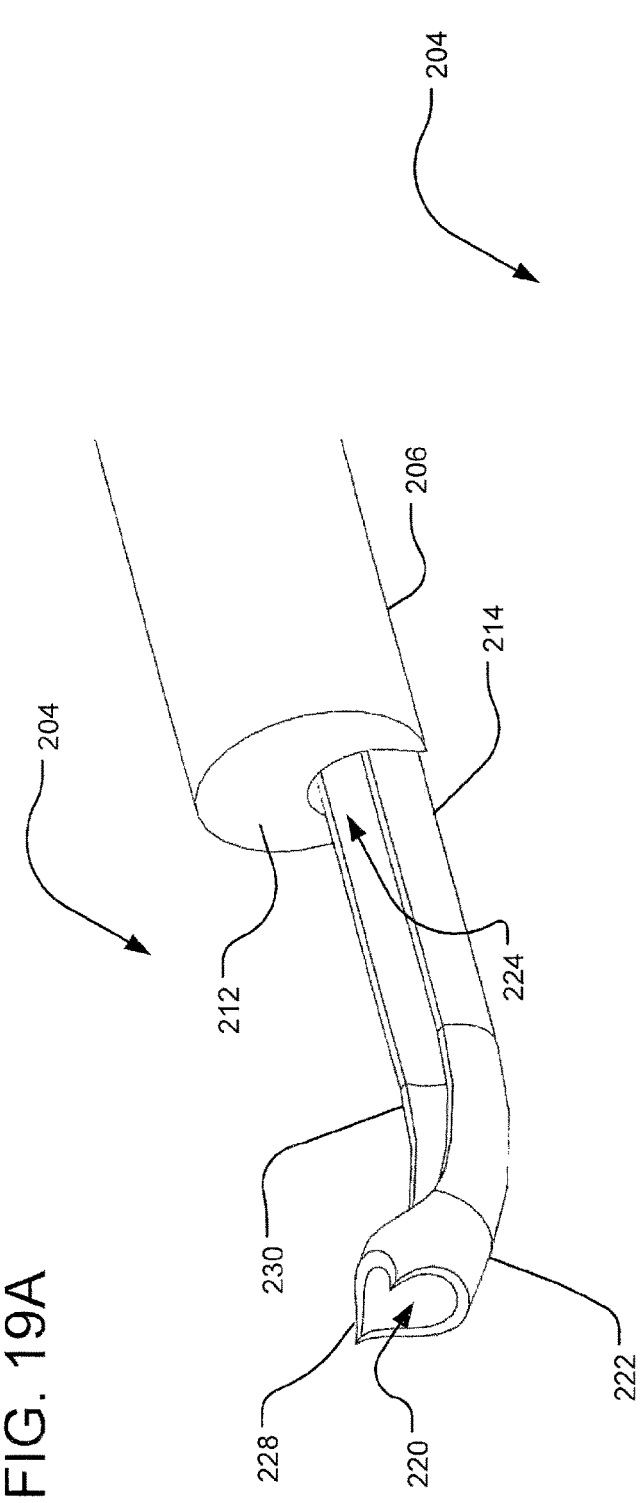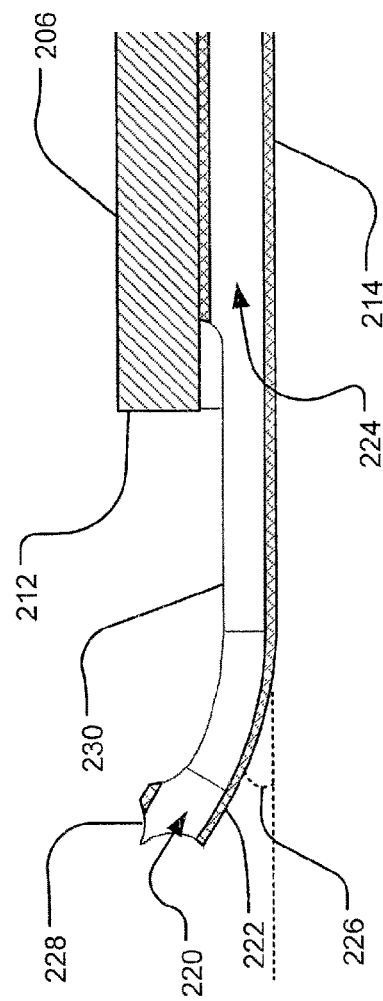
FIG. 19A
FIG. 19B

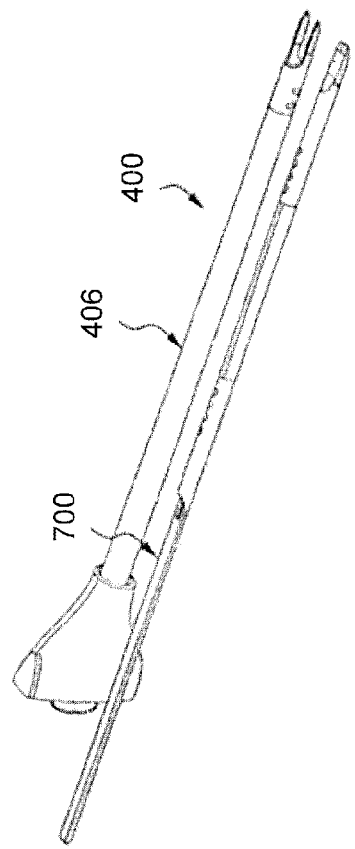
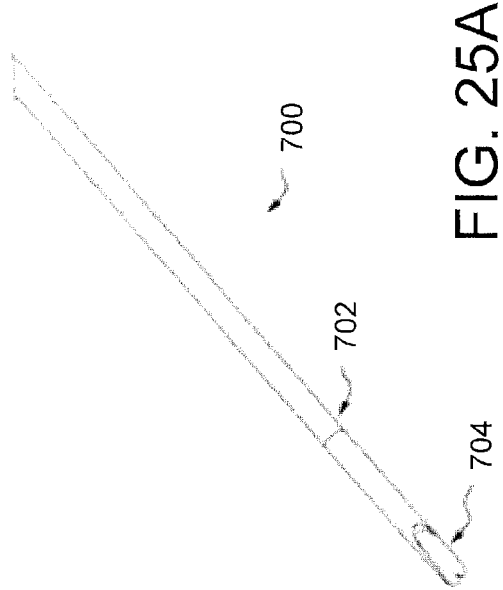
FIG. 25B
FIG. 25A

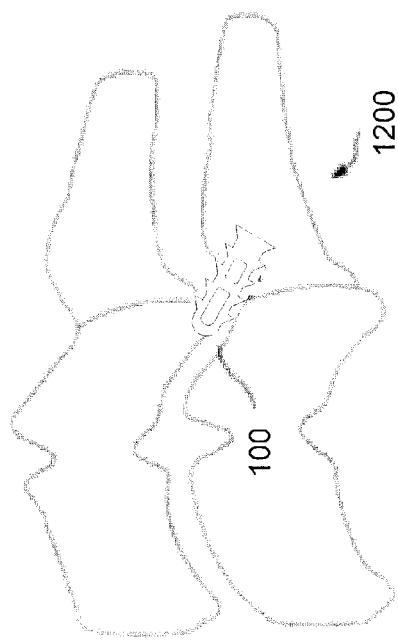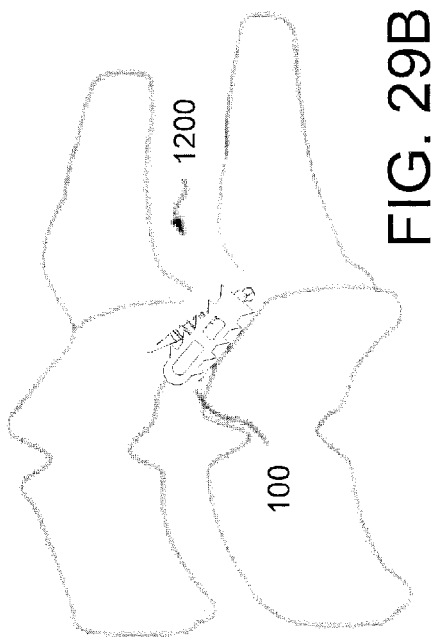

APPARATUS AND METHOD FOR BONE SCREW DEPLOYMENT

CROSS-REFERENCE TO RELATED APPLICATIONS

The present application claims priority under 35 U.S.C. § 119 to U.S. provisional patent application 61/734,832, which was filed Dec. 7, 2012 and entitled "Bone Screw Deployment Device," and to U.S. provisional patent application 61/766,186, which was filed Feb. 19, 2013 and entitled "Bone Screw Deployment Device."

Each of the aforementioned applications is hereby incorporated by reference in its entirety into the present application.

TECHNICAL FIELD

Aspects of the present disclosure relate to a device for distracting the spine and more particularly to a tool for distracting a facet joint of the spine, an implant for maintaining the distracted position of the joint, and a device for deploying a bone screw to anchor the implant.

BACKGROUND

Chronic back problems cause pain and disability for a large segment of the population. Adverse spinal conditions may be characteristic of age. In particular, spinal stenosis (including, but not limited to, central, canal, and lateral stenosis) and facet arthropathy may increase with age. Spinal stenosis results in a reduction of foraminal area (i.e. the available space for the passage of nerves and blood vessels), which may compress cervical nerve roots and cause radicular pain. Both neck extension and ipsilateral rotation, in contrast to neck flexion, may further reduce the foraminal area and contribute to pain, nerve root compression, and neural injury.

Cervical disc herniations may be a factor in spinal stenosis and may predominantly present upper extremity radicular symptoms. In this case, treatment may take the form of closed traction. A number of closed traction devices are available that alleviate pain by pulling on the head to increase foraminal height. Cervical disc herniations may also be treated with anterior and posterior surgery. Many of these surgeries are performed through an anterior approach, which requires a spinal fusion. These surgeries may be expensive and beget additional surgeries due to changing the biomechanics of the neck. There is a three percent incidence of re-operation after cervical spine surgery. Moreover, these surgeries may be highly invasive leading to long recovery times.

There is a need in the art for implants, delivery systems, and methods of implantation that facilitate the fusion of a spinal facet joint via a minimally invasive or percutaneous procedure from, for example, a posterior approach.

It is with these observations in mind, among others, that various aspects of the present disclosure were conceived and developed.

SUMMARY

Implementations described and claimed herein address the foregoing problems, among others, by providing a bone anchor deployment device. In one implementation, the bone anchor deployment device includes a flexible shaft extending from a proximal end to a distal end. The flexible shaft is adapted to bend along a deployment trajectory. A socket at the distal end of the flexible shaft is adapted to retain a bone anchor in a non-coaxial position. The bone anchor deployment device further includes a guide shaft having a lumen and a distal tip and an elongated tube extending through at least a portion of the guide shaft lumen and protruding from the distal tip of the guide shaft. A guide passage extends through a lumen of the elongated tube, and a channel is formed from one or more surfaces at a distal end of the guide passage. The channel is oriented at an angle relative to the guide passage and is adapted to cause the flexible shaft to bend. A window is disposed at a distal end of the channel. The window provides an opening in the elongated tube to the guide passage. The channel and the guide passage form the deployment trajectory through the window.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIG. 3A is perspective view of a longitudinal cross-section of the distal end of the deployment guide of FIG. 2.

FIG. 3B is a bottom perspective view of the distal end of the deployment guide of FIG. 2.

FIG. 19A illustrates a perspective view of a distal end of the deployment guide of FIG. 18.

FIG. 19B displays a side view of a longitudinal cross-section of the distal end of the deployment guide of FIG. 18.

FIGS. 25A and 25B display perspective views of example access chisels and the guide tube of FIG. 8.

FIGS. 29A and 29B show the implant during and after insertion into the facet joint, respectively.

DETAILED DESCRIPTION

Figure 1:
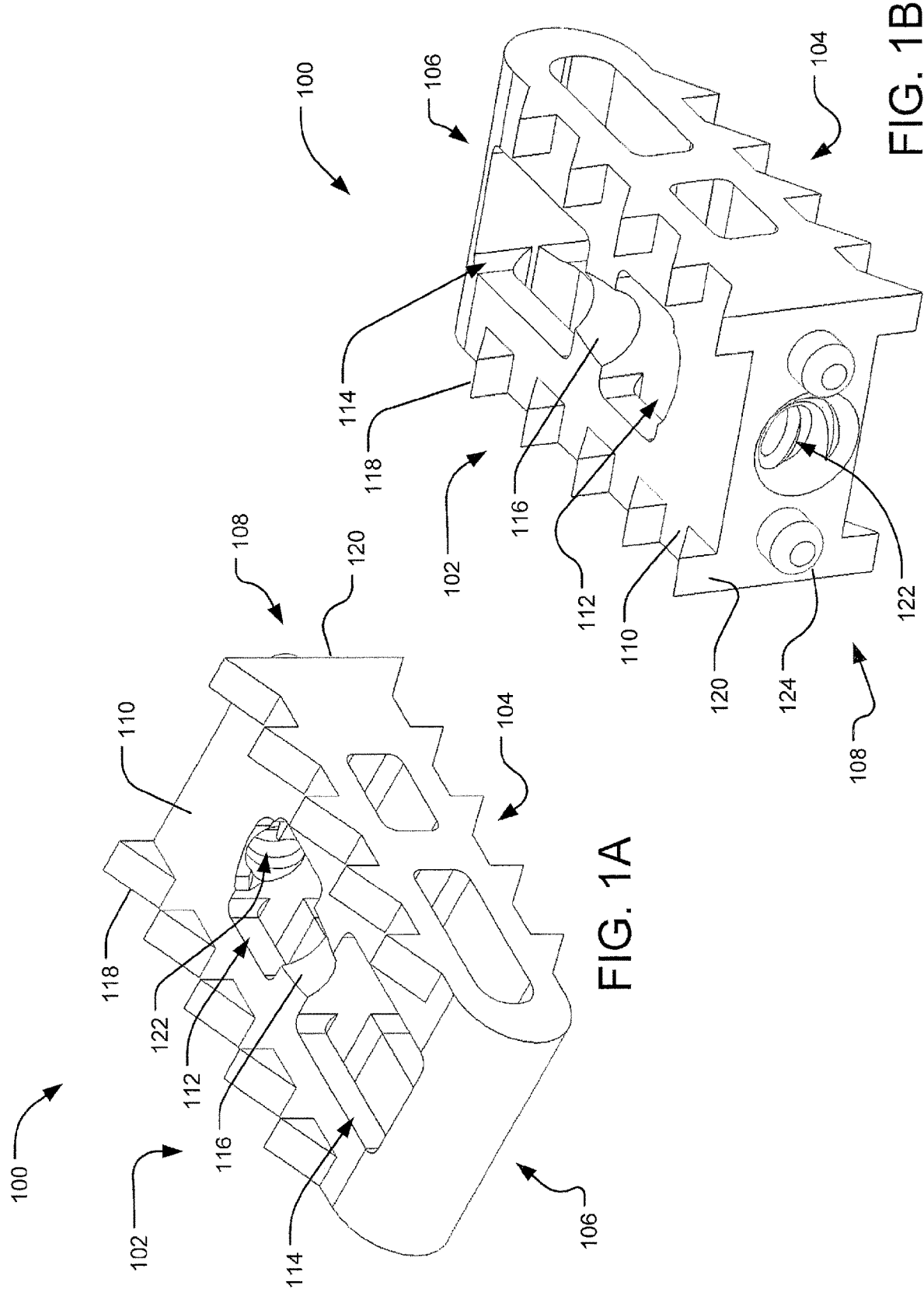
FIGS. 1A and 1B are distal and proximal isometric views, respectively, of an example spinal facet cage implant.

Aspects of the present disclosure generally involve devices and methods for treating spinal stenosis. Spinal stenosis reflects a narrowing of one or more areas of the spine often in the upper or lower back. This narrowing can put pressure on the spinal cord or on the nerves that branch out from the compressed areas. Individual vertebrae of the spine are positioned relative to each other and their separation is maintained by discs separating main vertebral bodies and by capsules positioned within facet joints. The discs and capsules are separated from the bone of their respective joints by cartilage. Spinal stenosis is often indicative of degeneration of a disc, a capsule, or the cartilage in a joint, which leads to a compression of the joints and the narrowing mentioned.

As such, in one aspect, a device for distracting a facet joint of the spine is provided to remedy this condition. The device may include a tool and an implant for distracting and maintaining the distracted position of the joint. The device may be adapted to access a facet joint by inserting a delivery tool and an implant, forcibly separate the associated articular surfaces with the tool, the implant, or both, and leave the implant in place to maintain the separation of the articular surfaces. This approach may allow for maintaining the distraction of the joint, thereby relieving symptoms associated with spinal stenosis.

In one particular aspect, a spinal facet cage implant sized for implantation in a spinal facet joint to bring about the fusion of the spinal facet joint is provided. To deploy the implant into the spinal facet joint space, a distraction system is provided. The distraction system is configured to minimally invasively or percutaneously deliver the implant into the spinal facet joint, for example, via a posterior approach. The distraction system includes a deployment guide, a release driver, and a bone screw driver.

After an initial distraction is provided via, for example, insertion of a chisel, a guide tube, or other delivery device to maintain the initial distraction at a percutaneous access site, the superior and inferior surface of the joint is decorticated and prepared. The deployment guide is inserted into the guide tube. The implant is interfaced with or otherwise attached to a distal end of an elongated tube extending from a lumen of a shaft of the deployment guide. To retain the implant in an attached manner to the deployment guide, the release driver is fully inserted through a guide passage extending through a lumen of the elongated tube, and a threaded member of a flexible shaft of the release driver engages the implant through a window providing an opening in the elongated tube to the guide passage. A threaded hole in the implant matingly receives the threaded member of the flexible shaft of the release driver. A channel, formed from a contoured or angled surface in the distal end of the guide passage, causes the flexible shaft of the release driver to bend, such that the implant is retained in tension. The window is disposed at the distal end of the guide passage relative to the channel.

Inserting the deployment guide into the guide tube delivers the implant into the spinal facet joint. In some cases, malleting may be needed to fully engage the implant with the joint. The implant may have teeth or other engaging features to engage surfaces of the joint. The threaded member of the flexible shaft is released from the implant, and the release driver is withdrawn from the deployment guide, leaving the implant in the joint.

To anchor the implant in the joint, a bone screw is delivered into the implant by inserting the bone screw driver into the deployment guide. The bone screw driver includes a collet interfaced with a bone screw. Stated differently, a rounded head of the bone screw is retained in a socket of the collet by retracting the collet proximally into a retaining ring of a flexible shaft at a distal end of the bone screw driver, thereby tightening the socket to retain the bone screw head. The collet retains the bone screw regardless of the axial alignment. As the bone screw approaches the window of the elongated tube, the channel causes the flexible shaft of the bone screw collet drive to bend along the contoured or angled surface in the distal end of the guide passage. The channel and the window guide the bone screw along a deployment trajectory into the threaded hole of the implant. Once the bone screw is deployed into the implant, thereby anchoring the implant in the joint, the collet releases the bone screw head, and the bone screw driver, the deployment guide, and the guide tube are withdrawn from the percutaneous access site.

It will be appreciated that although the implementations are described herein with reference to apparatuses and methods from implanting an implant in the facet space of the cervical spine, the presently disclosed technology may be used to deliver an implant into the facet space in the lumbar or thoracic spine. Further, the presently disclosed technology may be used to implant an implant in the disc space of the cervical, thoracic, or lumbar spine. For example, the implant may be a lateral lumbar or anterior cervical cage that may be implanted in the disc space. It will be understood that the deployment guide and bone screw driver described herein may be standalone tools or used in conjunction with a variety of other tools.

For a detailed description of an example spinal facet cage implant 100, reference is made to FIGS. 1A and 1B, which are distal and proximal isometric views, respectively.

The implant 100 may be formed of a bone or bone substitute material or a biocompatible metal, ceramic, polymer, or some combination thereof. In one implementation, the implant 100 includes a first face 102 generally opposite a second face 104. The first and second faces 102 and 104 extend longitudinally between a distal leading end 106 and a proximal trailing end 108.

In one implementation, the first face 102 includes a generally planar surface 110 having one or more windows or openings (e.g., a proximal window 112 and a distal window 114) defined therein. The proximal and distal windows 112 and 114 may be opposed or otherwise defined relative to respective windows defined in a surface of the second face 104. The implant 100 may have windows of any shape, size, number, and orientation. In one implementation, the surface 110 of the first face 102 includes a groove 116 defined therein for receiving an anchor, such as a bone screw (e.g., the bone screw shown in FIG. 12), to secure the implant 100 in the spinal facet joint. Further, the first and second faces 102 and 104 may include textured features 118 that provide friction between the spinal facet joint and the implant 100. It will be appreciated by those skilled in the art that the textured features 118 may be a variety of shapes, sizes, number, orientation, textures, or the like. For example, as shown in FIGS. 1A and 1B, the features 118 may be uni-directional teeth or bards for preventing the implant 100 from proximally self-displacing in the facet joint once implanted therein.

Figure 12:
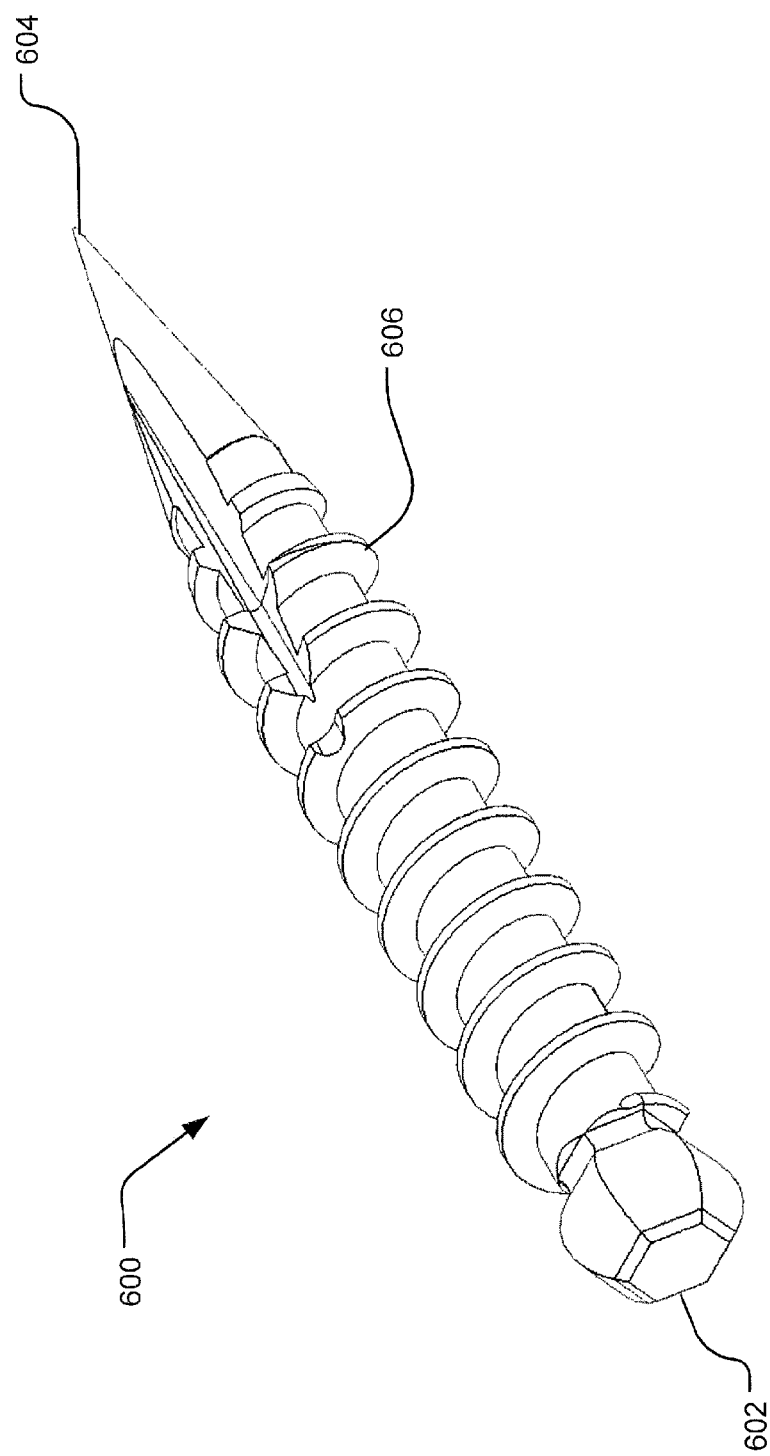
FIG. 12 illustrates a proximal perspective view of an example bone screw.

In one implementation, the proximal trailing end 108 includes a surface 120 having a hole 122 defined therein with engaging features (e.g., threaded features) for coupling to a release driver (e.g., the release driver shown in FIG. 5) and/or for engaging a bone screw (e.g., the bone screw shown in FIG. 12). The hole 122 extends through the implant 100 at an angle relative to the surface 110 such that a screw or other anchor extends through the hole 122 and along the groove 116, as illustrated, for example, in FIGS. 22 and 23. The proximal surface 120 may further include a pair of cylindrical pegs 124 with rounded edges. In one implementation, the hole 122 is generally centered on the proximal surface 120, and the pegs 124 generally oppose each other on either side of the hole 122.

Figure 2:
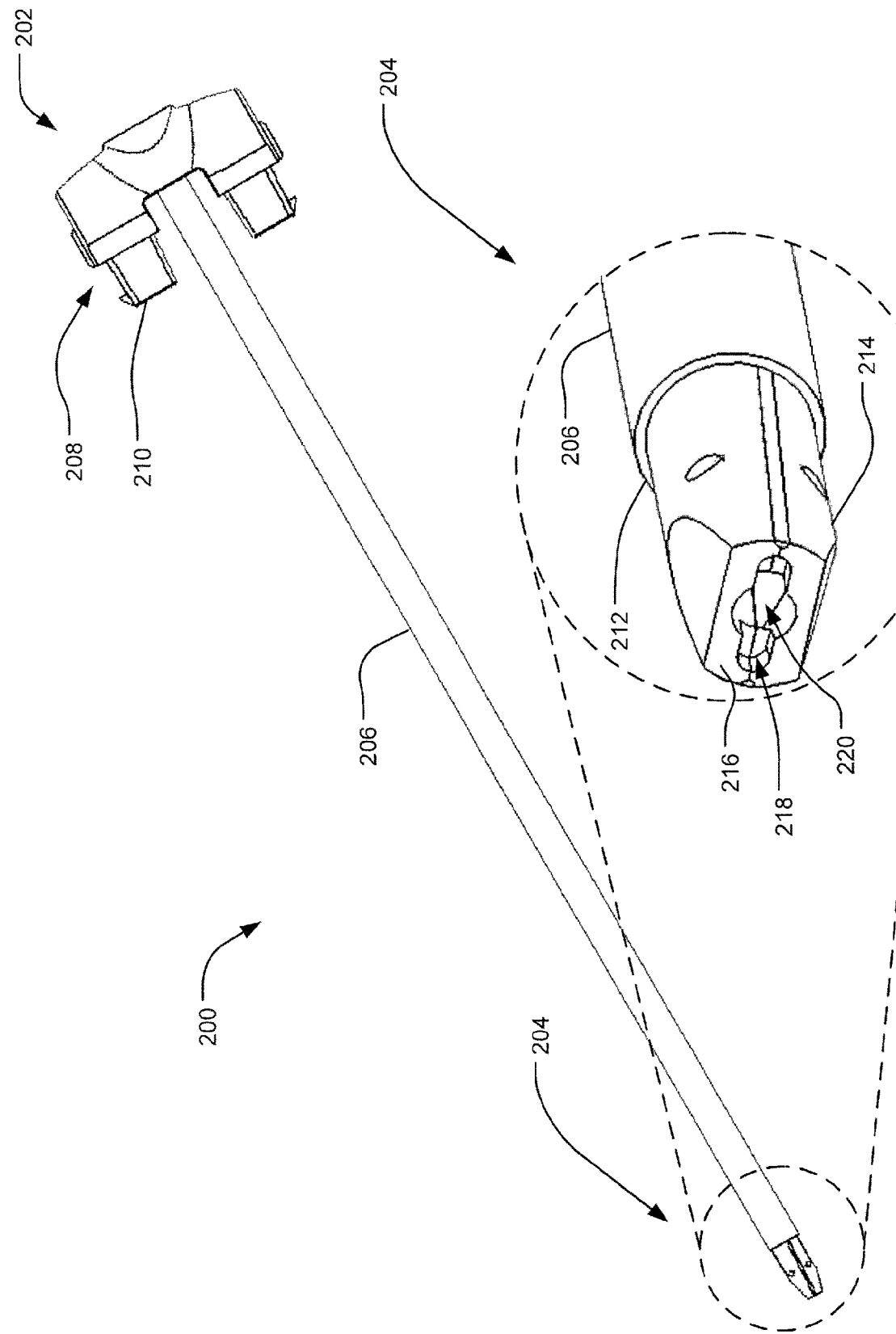
FIG. 2 shows a perspective view of an example deployment guide and a detailed view of a distal end of the deployment guide.
Figure 4:
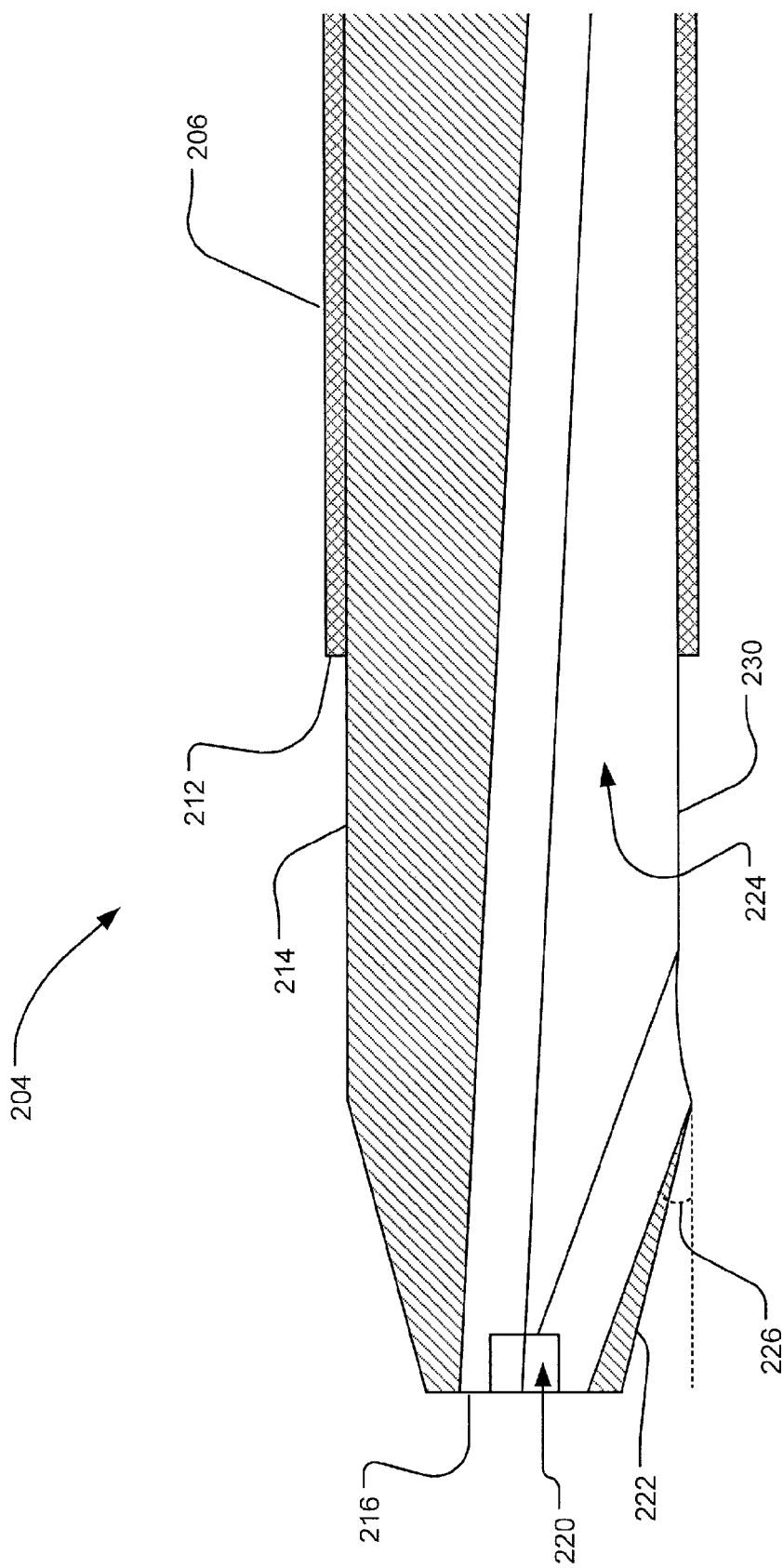
FIG. 4 is a side view of a longitudinal cross-section of the distal end of the deployment guide of FIG. 2.

Turning to FIGS. 2-4, a detailed description of an example deployment guide 200 extending from a proximal trailing end 202 to a distal leading end 204 is provided. In one implementation, the deployment guide 200 includes a guide shaft 206 with a handle assembly 208 at the proximal end 202. The handle assembly 208 may further include one or more male members 210 for engaging a guide tube or tool (e.g., via the male members 210 being received in female receiving portions 410 of the guide tool 400 shown in FIG. 8).

In one implementation, the distal end 204 of the deployment guide 200 includes an elongated tube 214 extending through a lumen of the guide shaft 206 and protruding from a distal tip 212 of the guide shaft 206. The elongated tube 214 includes a distal surface 216 adapted to receive the proximal surface 120 of the implant 100. In one implementation, the distal surface 216 of the elongated tube 214 includes one or more holes 218 and a window 220 defined therein. The holes 218 and window 220 may be adapted and oriented relative to the pegs 124 and hole 122 of the implant 100, respectively. Stated differently, the holes 218 may be adapted to receive the pegs 124, and the window 220 may have a centerline that is coextensive with a centerline of the hole 122 to provide a deployment trajectory from the deployment guide 200 to the implant 100.

As can be understood from FIGS. 3A, 3B, and 4, in one implementation, the elongated tube 214 includes a guide passage 224 extending through a lumen of the elongated tube 214. The guide passage 224 includes an inner diameter adapted to permit passage of one or more delivery tools, for example, features of the release driver shown in FIG. 5-7 and/or of the bone screw driver shown in FIGS. 9-14. The window 220 provides an opening in the elongated tube 214 to the guide passage 224.

In one implementation, the distal end of the guide passage 224 includes one or more angled or contoured surfaces, which form a channel 222. The guide passage 224, the channel 222, and the window 220 form a deployment trajectory through the hole 122 of the implant 100. In one implementation, the channel 222 is oriented at an angle 226 between approximately 15° and 45° relative to the guide passage 224. The deployment trajectory, including the window 220, the angle 226 of the channel 222, and the inner diameter of the guide passage 224, is adapted to position an anchor, such as the bone screw shown in FIG. 12, at a proper deployment orientation in the implant 100.

As can be understood from FIG. 3B, in some implementations, the elongated tube 214, includes one or more slots or openings 230 running along a longitudinal length of the elongated tube 214. The slots 230 may facilitate manufacturing of the elongated tube 214.

Figure 5:
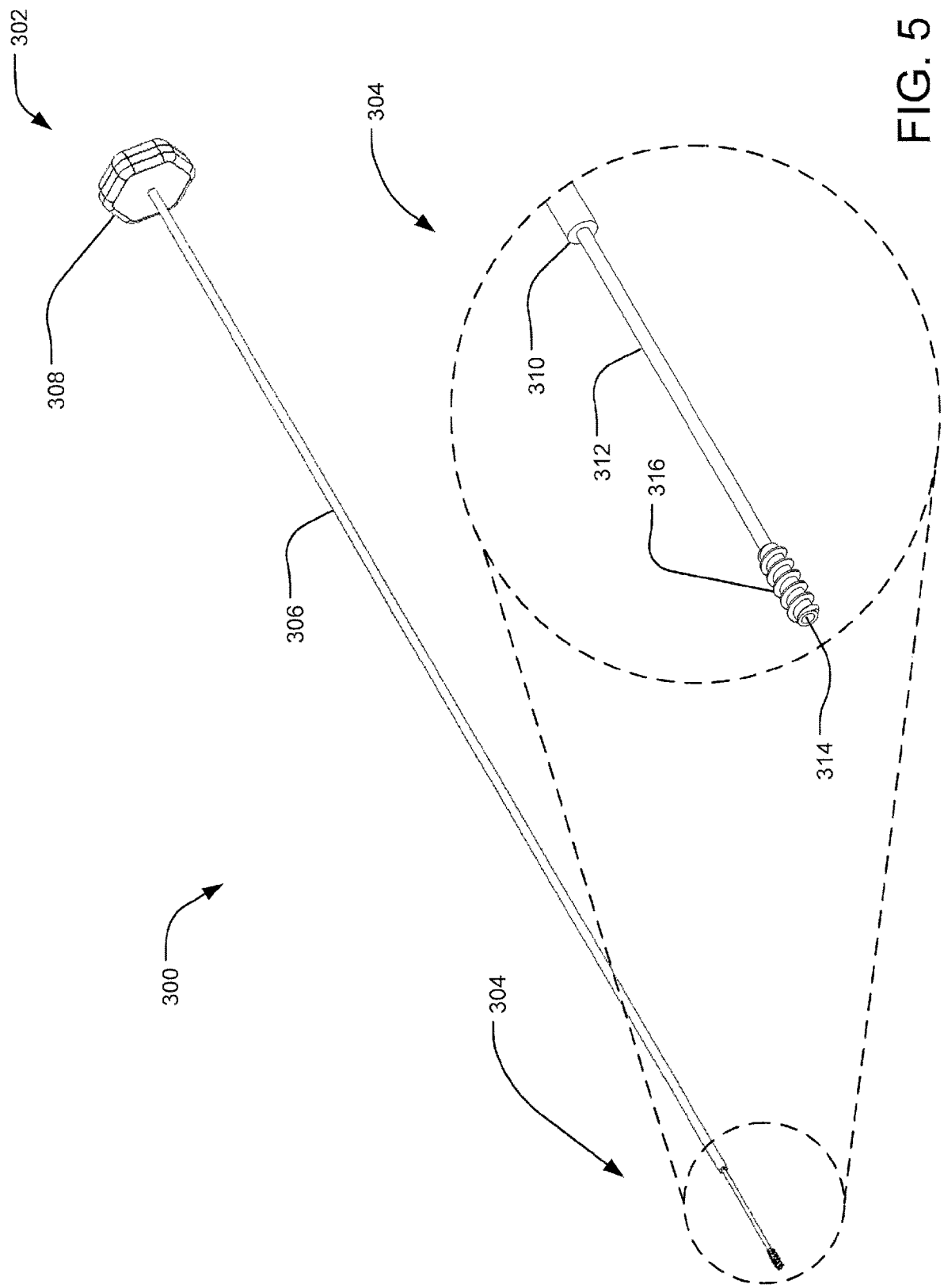
FIG. 5 illustrates a perspective view of an example release driver and a detailed view of a distal end of the release driver.

For a detailed description of an example release driver 300 extending from a proximal trailing end 302 to a distal leading end 304, reference is made to FIG. 5. In one implementation, the release driver 300 includes a shaft 306 with a handle 308 at the proximal end 302 and a distal tip 310 at the distal end 304.

Figure 6:
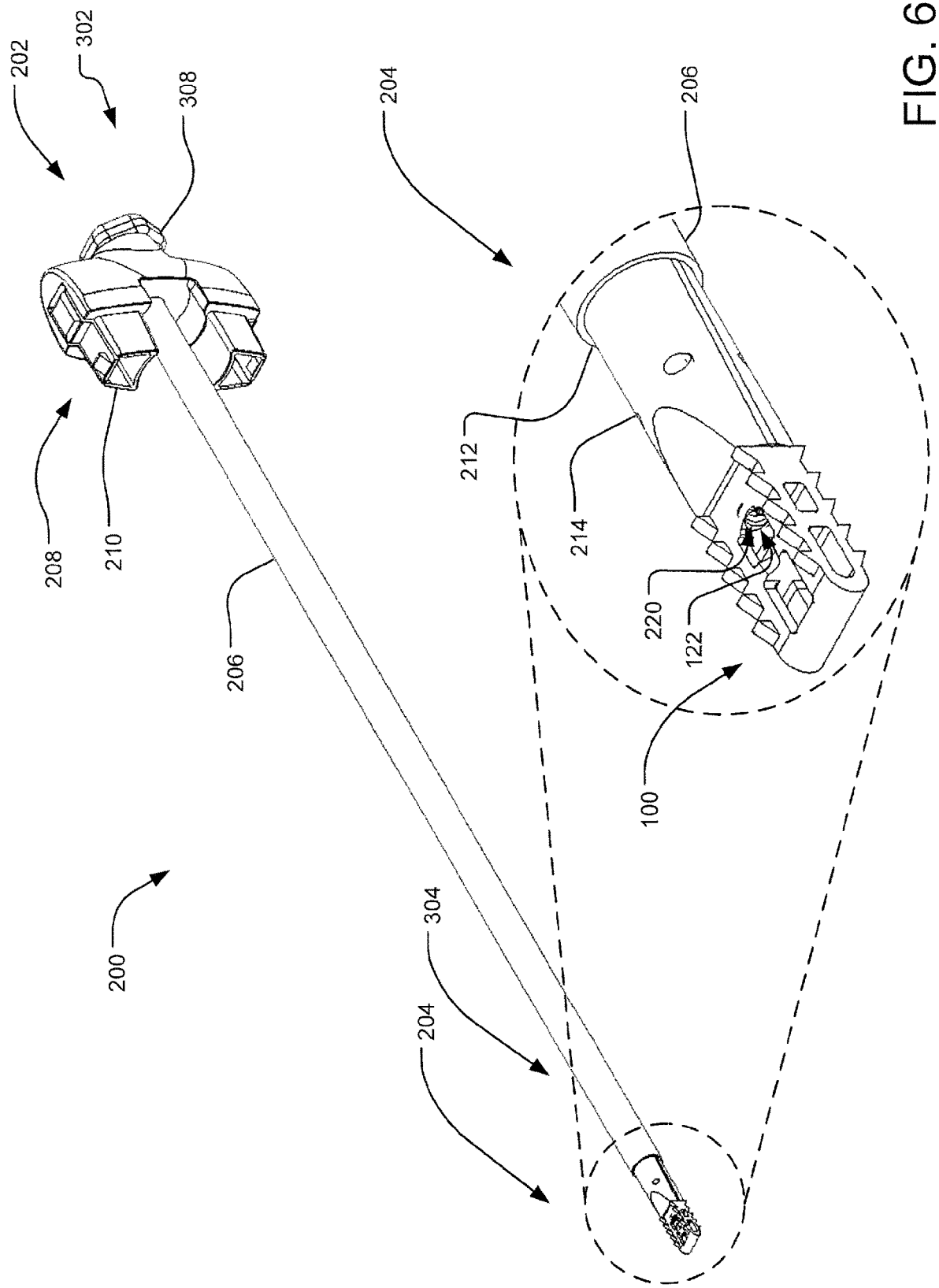
FIG. 6 is a perspective view and a detailed view of the distal end of the deployment guide of FIG. 2 coupled to a proximal end of the implant.
Figure 7:
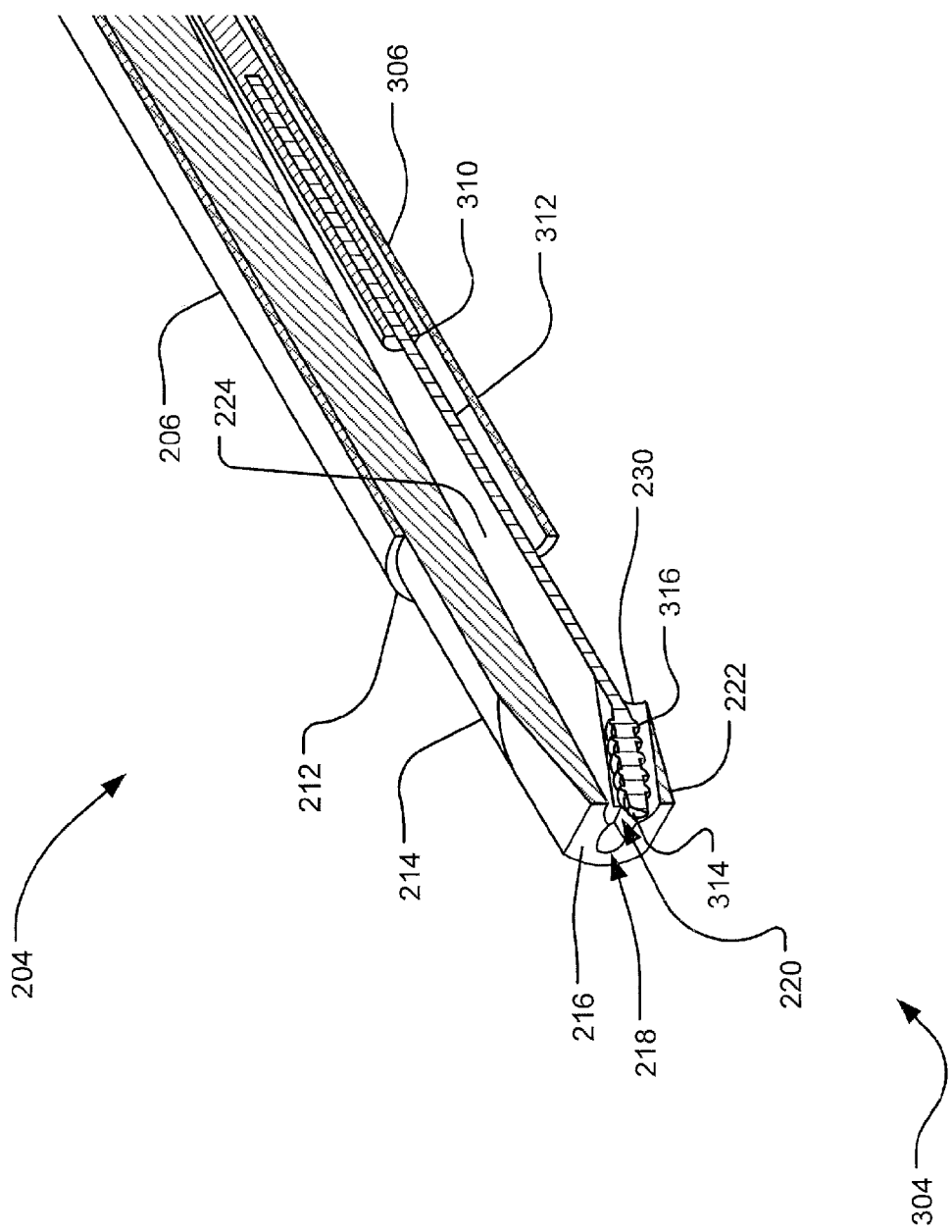
FIG. 7 shows a perspective view of a longitudinal cross-section of the release driver of FIG. 5 approaching the distal end of the deployment guide of FIG. 2, wherein a flexible screw shaft of the release driver bends along a channel as it approaches an opening in an elongated tube of the distal end of the deployment guide.

As can be understood from FIGS. 5-7, the release driver 300 may be used to release the implant 100 from the deployment guide 200. Referring to FIG. 5, in one implementation, a flexible shaft 312 extends from the distal tip 310 of the shaft 306 and includes engagement features 316 at a distal tip 314 of the flexible shaft 312. The engagement features 316 may be any feature adapted to engage the hole 122 of the implant 100. For example, the engagement features 316 may be threaded members.

As shown in FIGS. 6 and 7, the implant 100 is interfaced with or otherwise attached to the distal surface 216 of the elongated tube 214. To retain the implant 100 in an attached manner to the deployment guide 200, the release driver 300 is fully inserted through the guide passage 224, such that the distal tip 314 extends through the window 220 to be received in the hole 122, and the engagement features 316 of the flexible shaft 312 of the release driver 300 engage complementary features of the hole 122. In other words, the hole 122 in the implant 100 is adapted to matingly receive the engagement features 316 of the flexible shaft 312 of the release driver 300.

The channel 222 causes the flexible shaft 312 of the release driver 300 to bend as shown in FIG. 7 as the distal tip 314 extends proximally from the window 220 along the guide passage 224. The bending of the flexible shaft 312 retains the implant 100 in tension. The bending or deflection of the shaft 312 allows the distal tip 314 to deflect into the implant hole 122 despite the implant hole 122 and the guide passage 224 not being axially aligned with each other.

Figure 8:
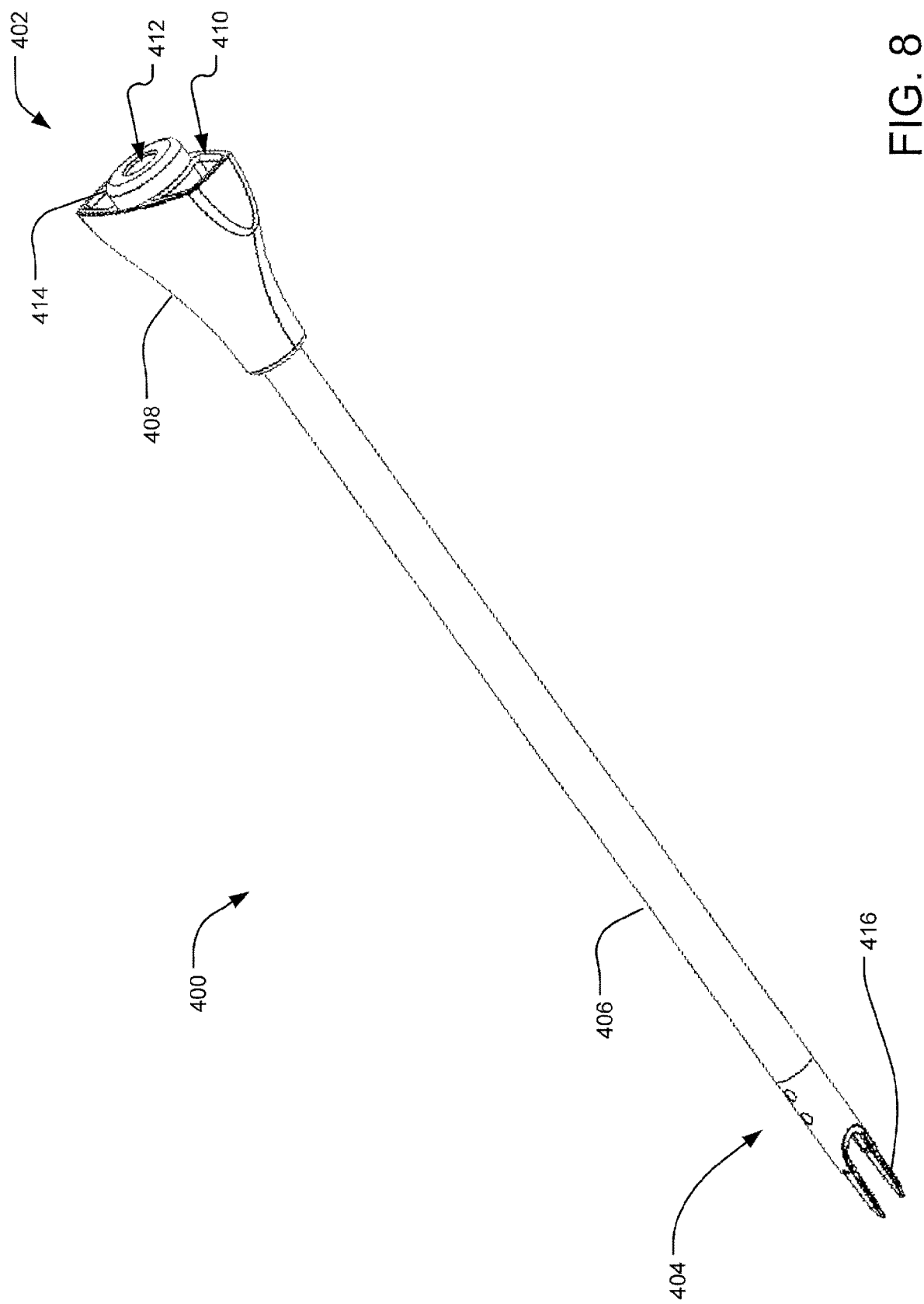
FIG. 8 illustrates a perspective view of an example guide tube or tool.

To facilitate the insertion of the implant 100 into the facet joint space, a guide tube 400, as shown in FIG. 8, is employed. In one implementation, the guide tube 400 extends from a proximal trailing end 402 to a distal leading end 404 and includes a tubular shaft 406 extending between a receiving assembly 408 and a pair of distal leading end anchoring forks 416. The receiving assembly 408 may include a female receiving portion 410 for receiving and engaging the male members 210 of the deployment guide 200. In one implementation, the receiving assembly 408 includes a raised surface 414 with a hole defined therein providing an opening to a lumen 412 extending through the tubular shaft 406.

In one implementation, the anchoring forks 416 may be textured distal parallel prongs for accessing a spinal facet joint and through which the deployment guide 200 may be routed to deliver the implant 100 in the facet joint. As illustrated in FIG. 8, in one implementation, the anchoring forks 416 are parallel prongs having the same height and configuration such that they are mirror images of each other. However, other arrangements are contemplated.

Inserting the deployment guide 200, interfaced with the implant 100 via the release driver 300, into the guide tube 400, delivers the implant 100 into the spinal facet joint. In some cases, malleting may be needed to fully engage the implant 100 with the joint.

After the implant is delivered to the facet joint, the engagement features 316 of the flexible shaft 312 is released from the implant 100, and the release driver 300 is withdrawn from the deployment guide 200, leaving the implant 100 in the joint.

To anchor the implant 100 in the joint, a bone screw 600 is delivered into the implant 100 by inserting a bone screw driver 500 into the deployment guide 200. For a detailed discussion of the bone screw driver 500 and bone screw 600, reference is made to FIGS. 9-14. The bone screw driver 500 is adapted to retain and drive the bone screw 600.

Figure 9:
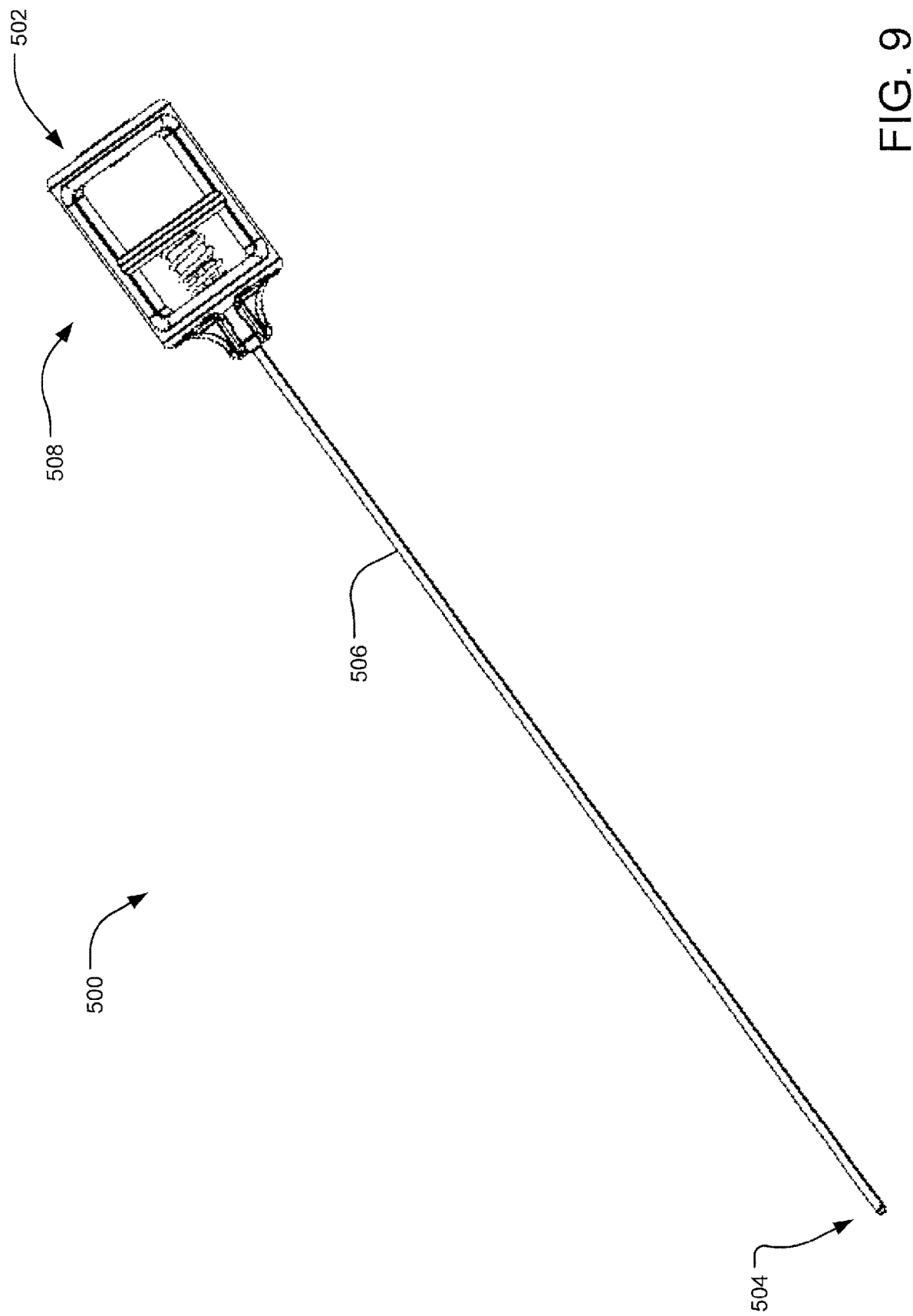
FIG. 9 shows a perspective view of an example bone screw driver.

As can be understood from FIG. 9, the bone screw driver 500 extends from a proximal trailing end 502 to a distal leading end 504. In one implementation, the bone screw driver 500 includes a flexible shaft 506 with a handle assembly 508 at the proximal end 502. It will be appreciated that although the shaft 506 is described herein as a flexible shaft, the shaft 506 may alternatively be a rigid shaft.

Figure 10:
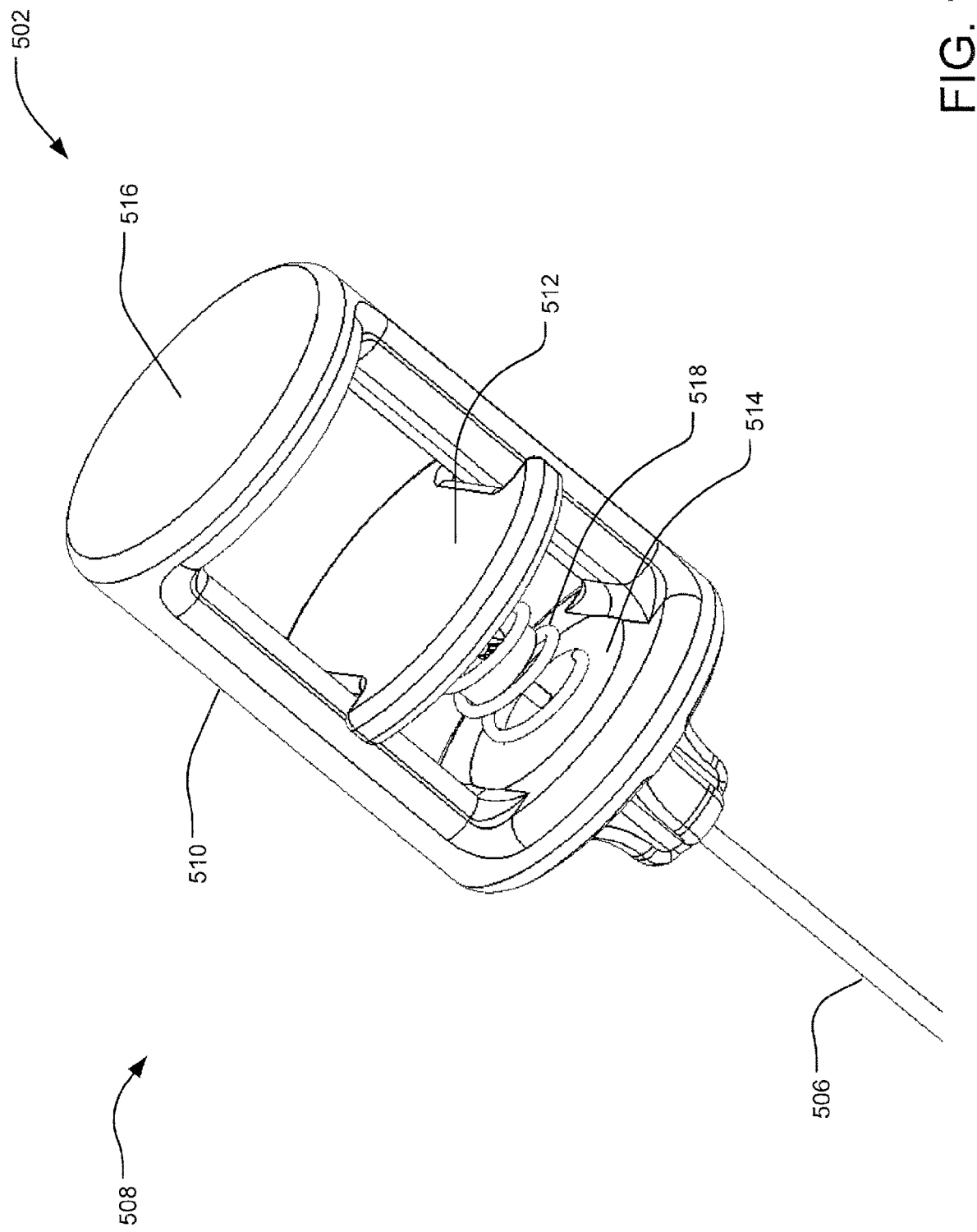
FIG. 10 is a detailed view of a handle assembly of the bone screw driver of FIG. 9.
Figure 11:
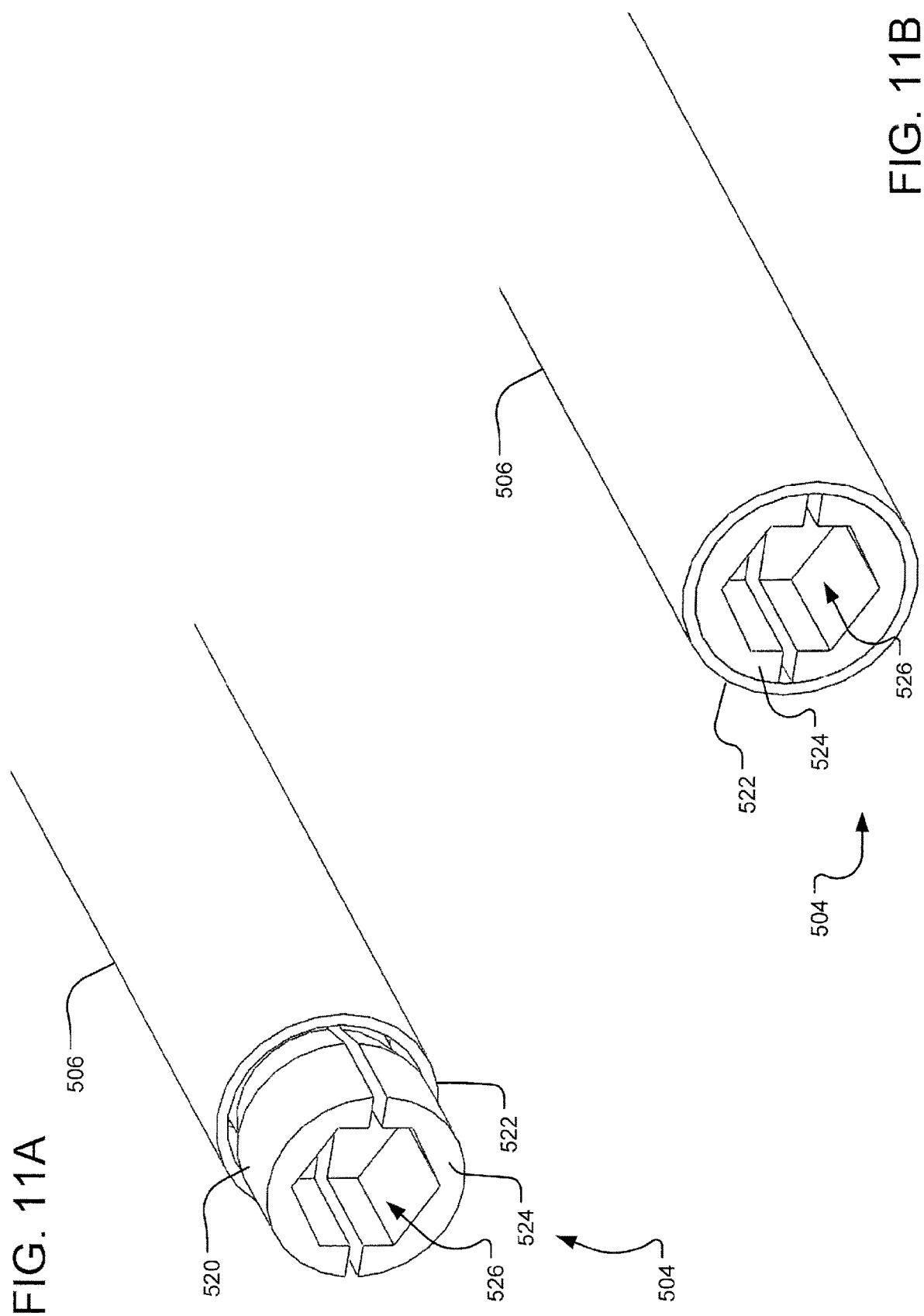
FIGS. 11A and 11B show a detailed view of a distal end of the bone screw driver of FIG. 9, with a collet in a released position and an engaged position, respectively.

Turning to FIG. 10, a detailed view of the handle assembly 508 is shown. In one implementation, the handle assembly 508 includes a sliding handle 512 adapted to slide longitudinally along members 510 extending between a distal surface 514 and a proximal surface 516. A spring 518 disposed around the flexible shaft between the distal surface 514 and the sliding handle 512 causes a collet 520 at the distal end 504 to move between a released position and an engaged position, as shown in FIGS. 11A and 11B, respectively. Biasing of the spring 518 causes the collet 520 to remain in one position, either the released position or engaged position, until the sliding handle 512 is pressed distally towards the distal surface 514.

As can be understood from FIGS. 11A and 11B, in one implementation, the distal end 504 of the bone screw driver 500 includes a retaining ring 522 at a distal end of the flexible shaft 506. The spring 518 causes the collet 520 to move relative to the retaining ring 522 as the sliding handle 512 is pressed and released. In one implementation, the collet 520 includes a distal surface 524 with a socket 526 defined therein. When the collet 520 is in the released position, the collet 520 extends from the retaining ring 522, such that the distal surface 526 is not coplanar with the retaining ring 522 and the socket 526 is relatively loose. When the collet 520 is in the engaged position, the collet 520 is retracted into the flexible shaft 506, thereby tightening the socket 520. In one implementation, the collet 520 is retracted into the flexible shaft 506, such that the distal surface 526 is generally coplanar with the retaining ring 522.

Figure 13:
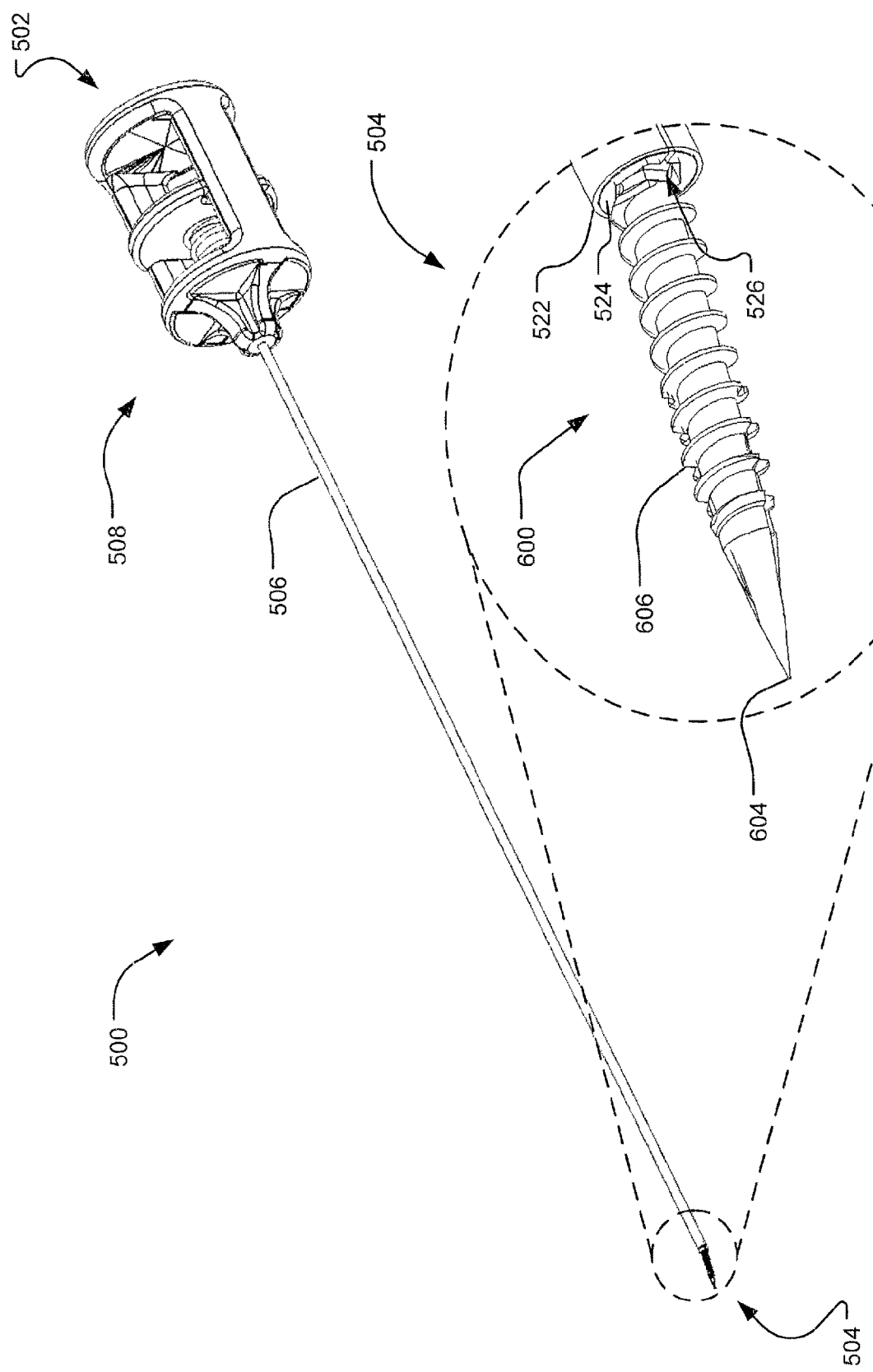
FIG. 13 shows a perspective view and a detailed view of the bone screw driver of FIG. 9, wherein the collet is interfaced with the bone screw.
Figure 14:
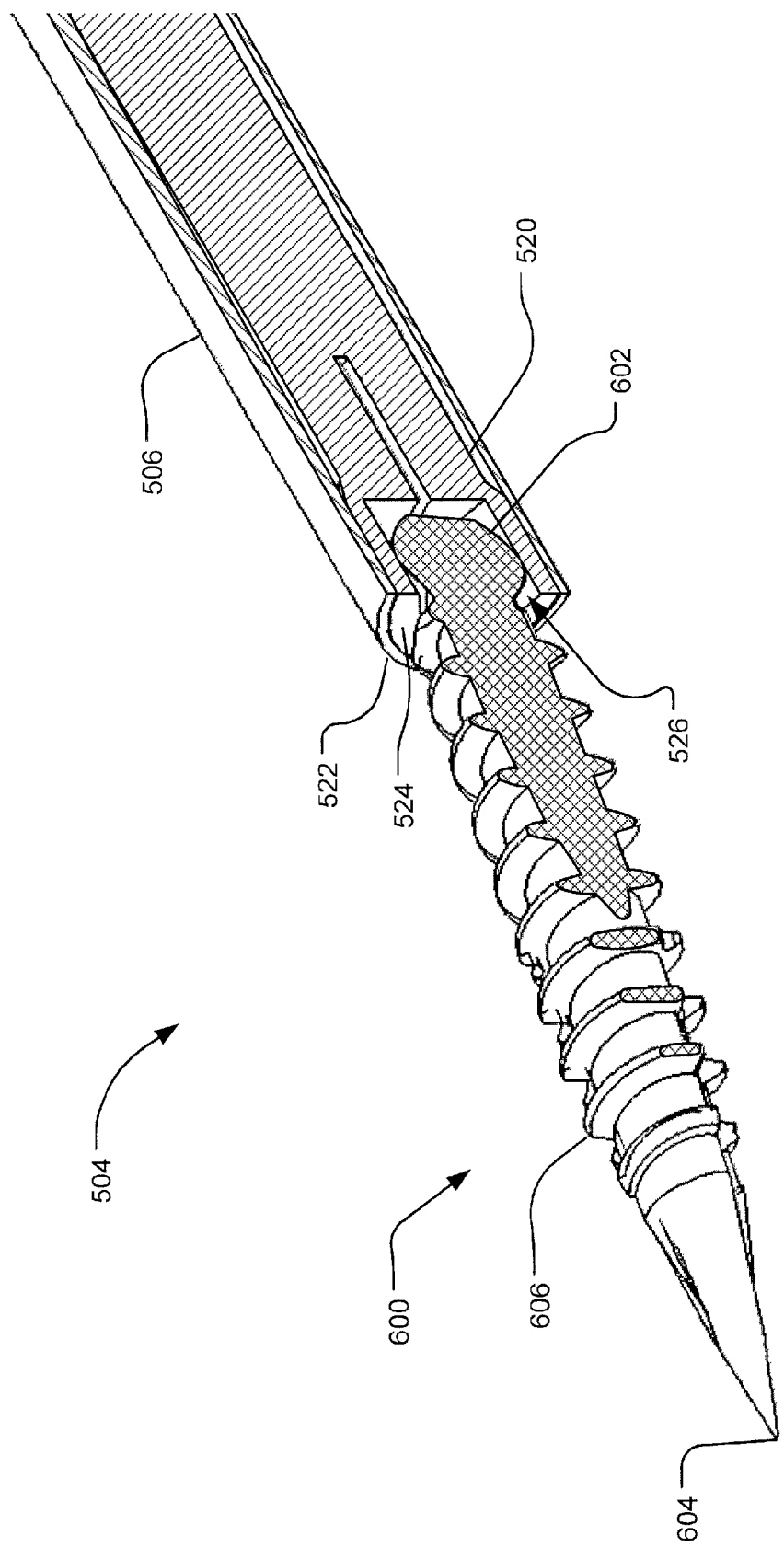
FIG. 14 displays a perspective view of a longitudinal cross-section of the bone screw driver of FIG. 9, wherein the collet is interfaced with the bone screw.

In one implementation, the socket 526 is adapted to receive and engage a head 602 of the bone screw 600. As shown in FIG. 12, the bone screw 600 includes engaging features 606 extending between the head 602 and a tip 604. The engaging features 606 may be a threaded member or any other features adapted to engage the hole 122 of the implant 100. Turning, to FIGS. 13-14, it will be appreciated that the head 602 of the bone screw 600 is retained in the socket 526 of the collet 520 by retracting the collet 520 proximally relative to the retaining ring 522 of the flexible shaft 506, thereby tightening the socket 526 to retain the bone screw head 602. In one implementation, the bone screw head 602 is a rounded knob, such that the bone screw head 602 is able to pivot within the socket 526 when retained in the engagement position. As such, the collet 520 retains the bone screw 600 regardless of the axial alignment.

In another implementation, rather than retaining the head 602 of the bone screw 600 with the collet 520, the bone screw driver 500 includes a suture that passes through the head 602 of the bone screw 600 and the flexible shaft 506 to the handle assembly 508. In this implementation, the bone screw 600 may be released by cutting or otherwise releasing the screw head 602 from the suture. In still another implementation, the bone screw driver 500 does not release the bone screw 600 and instead is adapted to break-away at the screw head 602 once the bone screw 600 mates with the implant 100, anchors into the bone in the joint, and reaches a torque.

Figure 15:
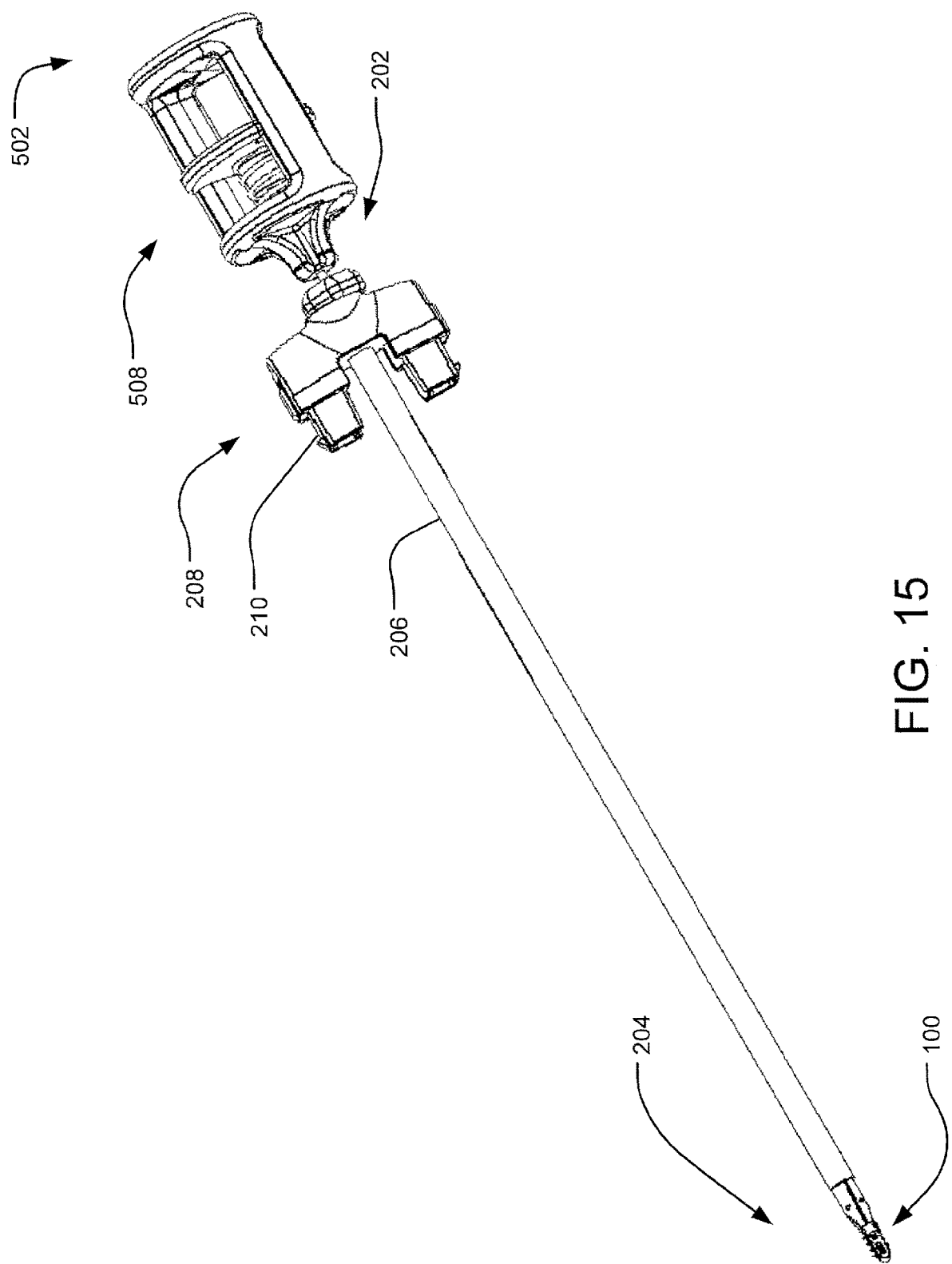
FIG. 15 is a perspective view of the bone screw driver of FIG. 9 inserted into the deployment guide of FIG. 2.
Figure 16:
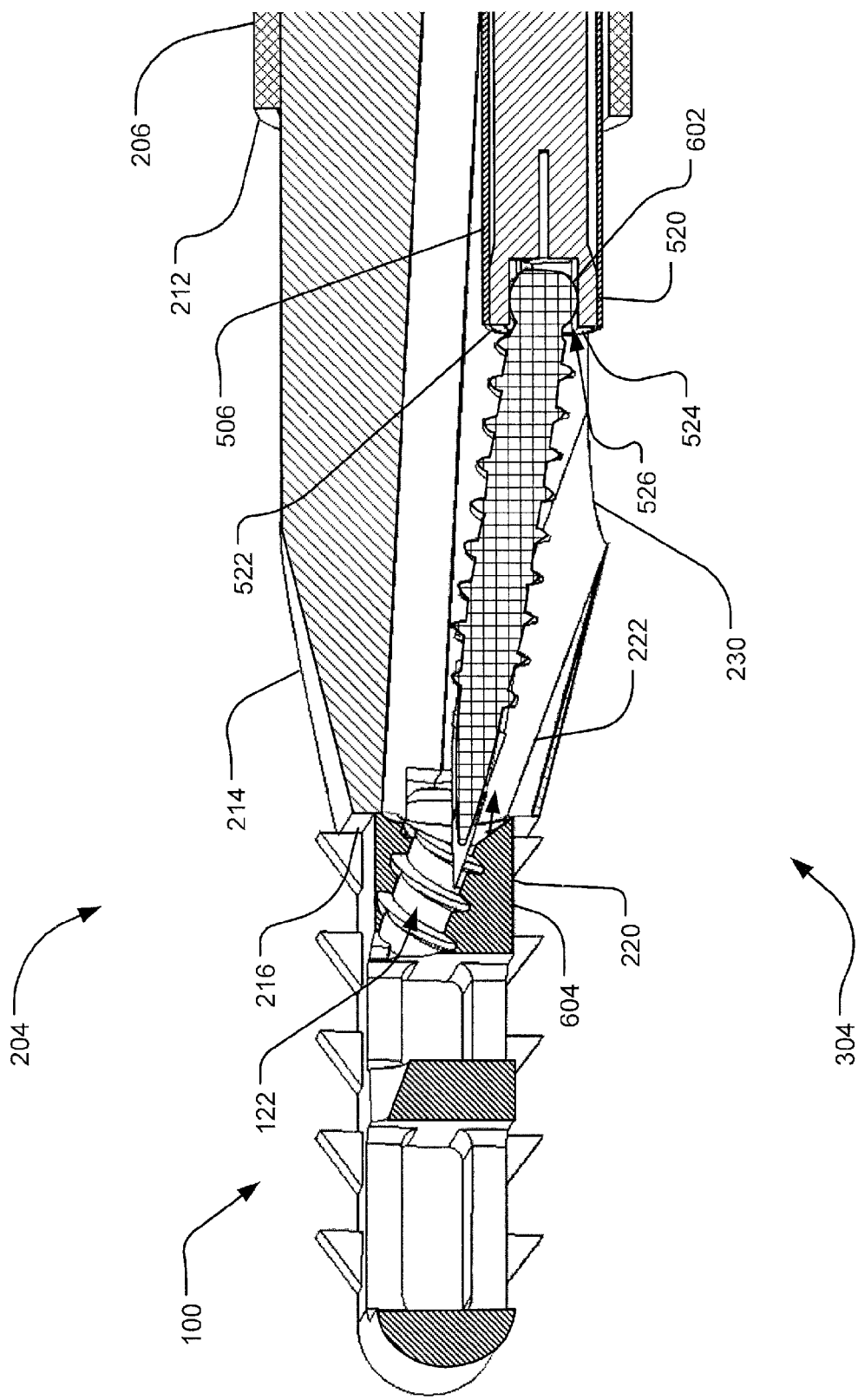
FIG. 16 is a side perspective view of a longitudinal cross-section of the bone screw interfaced with the bone screw driver of FIG. 9 approaching an opening in an elongated tube of the distal end of the deployment guide of FIG. 2 along a channel into a threaded hole in the implant.
Figure 17:
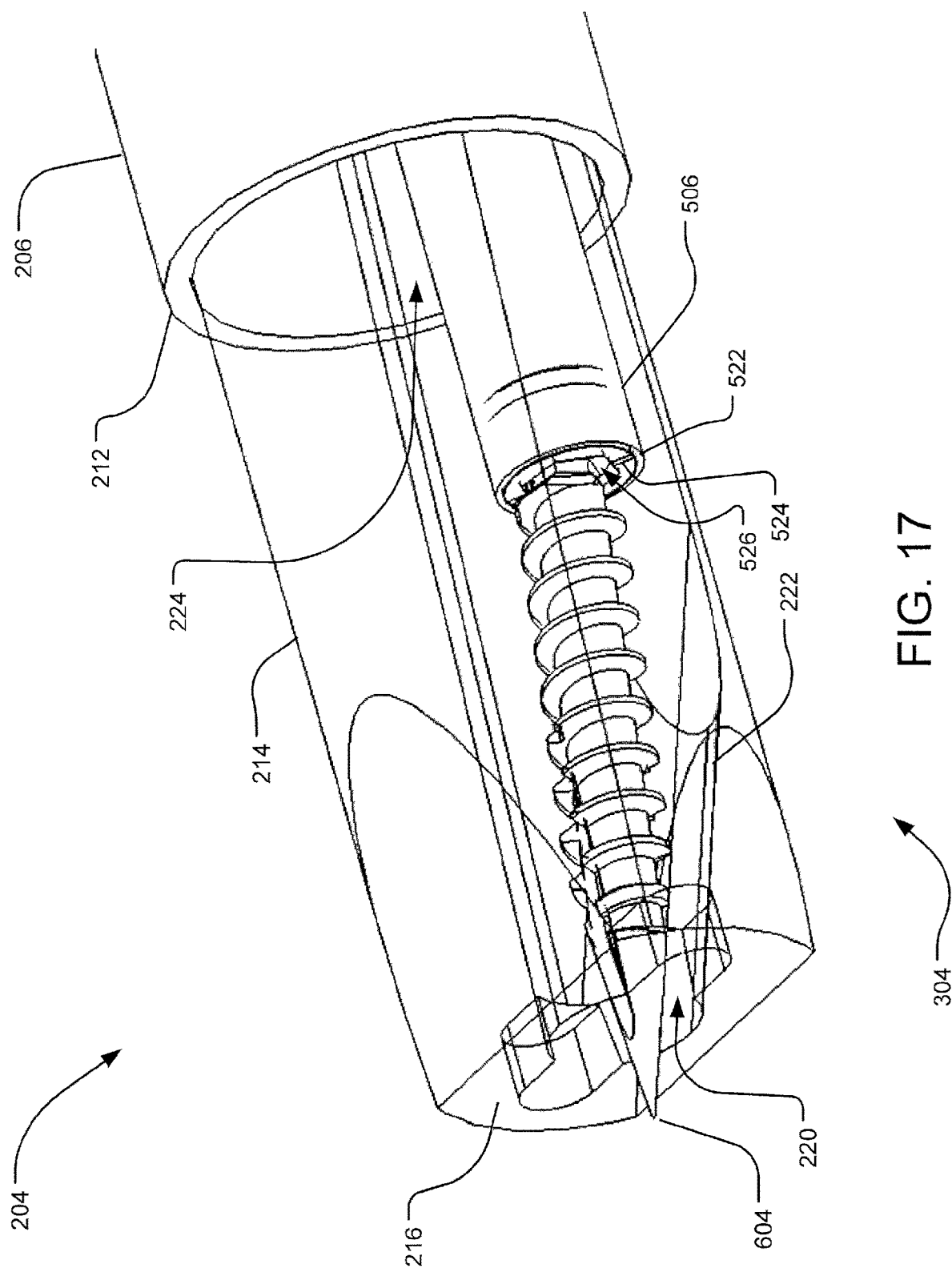
FIG. 17 is a side perspective view of the bone screw interfaced with the bone screw driver of FIG. 9 approaching an opening in an elongated tube of the distal end of the deployment guide of FIG. 2 along a channel, wherein the elongated tube is transparent for clarity.

As can be understood from FIGS. 15-17, the bone screw driver 500 is inserted through the lumen of the guide shaft 206 of the deployment guide 200 and guided along the guide passage 224 of the elongated tube 214.

As can be understood from FIGS. 13 and 14, in one implementation, the collet 520 interfaces and retains the bone screw 600 in a non-co-axial direction as the bone screw driver 500 advances the bone screw 600 through the guide passage 224 of the elongated tube 214. In other words, the bone screw tip 604 and longitudinal axis of the bone screw 600 are not coaxially aligned with the longitudinal axis of the flexible shaft 506 and as a result, the bone screw 600 is slightly tilted relative to the flexible shaft 506. As the tip 604 of the bone screw 600 approaches the window 220 of the elongated tube 214, the channel 222 causes the flexible shaft 506 of the bone screw collet drive 500 to bend along the contoured or angled surface in the distal end of the guide passage 224. In implementations where the bone screw 600 is tilted relative to the flexible shaft 506, the tilt will help the bone screw tip 604 enter the channel 222, as can be understood from FIG. 16. The channel 222 and the window 220 guide the bone screw 600 along a deployment trajectory into the hole 122 of the implant 100. The angle 226 of the channel 222 orients the bone screw 600 relative to the hole 122 to facilitate the delivery of the bone screw 600 into the implant 100 using the bone screw driver 500. For example, where the angle 226 the channel 222 is oriented at is between approximately 15° and 45° relative to the guide passage 224, the flexibility of the flexible shaft 506 and the retention of the bone screw 600 in a non-coaxial direction permits the bone screw 600 to be deployed between 0° and 45° of axial variation.

Figure 18:
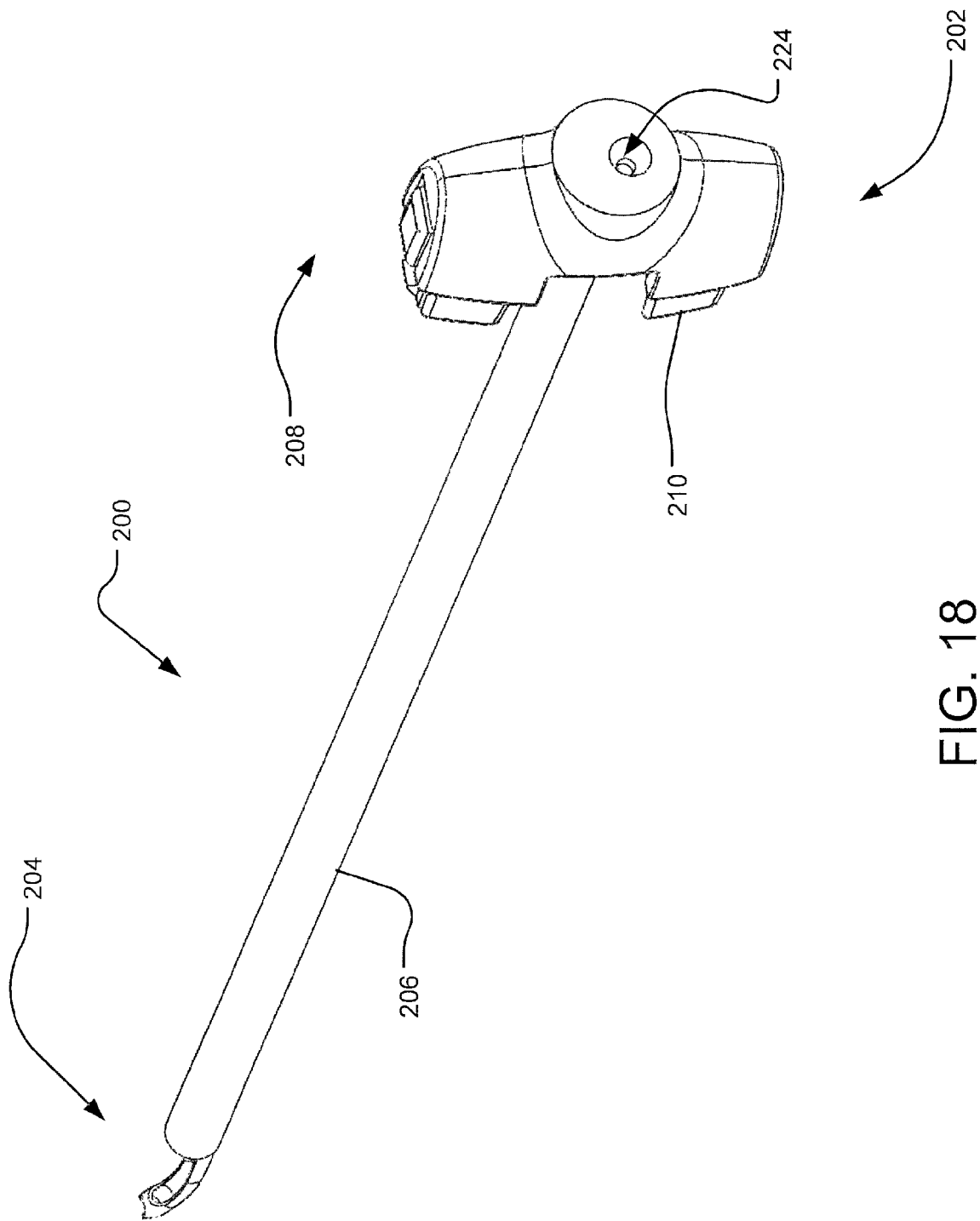
FIG. 18 shows a perspective view of another example of a deployment guide.
Figure 20:
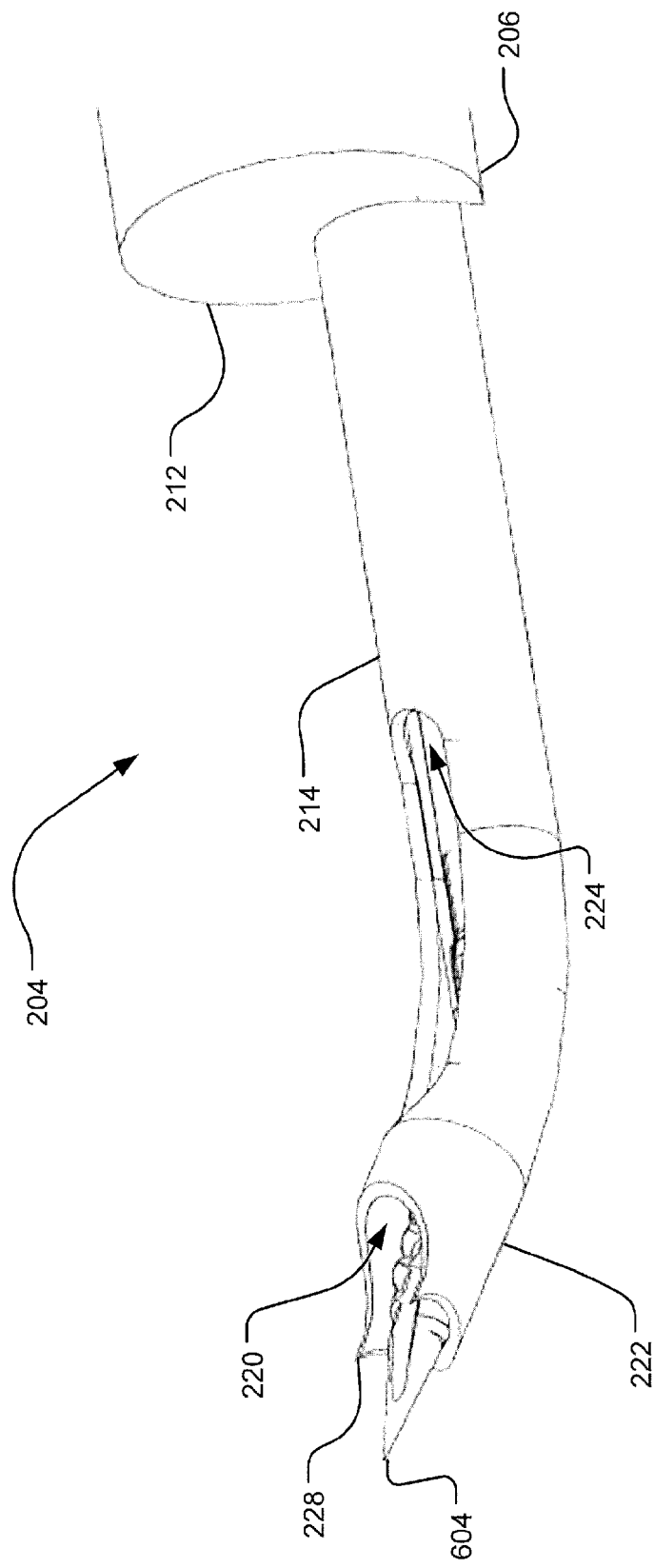
FIG. 20 shows a perspective view of the bone screw interfaced with the bone screw driver of FIG. 9 moving through an opening in an elongated tube of the distal end of the deployment guide of FIG. 18 along a channel.

Turning to FIGS. 18-20, another example of the deployment guide 200 extending from a proximal trailing end 202 to a distal leading end 204 is shown. In one implementation, the deployment guide 200 includes a guide shaft 206 with a handle assembly 208 at the proximal end 202. The handle assembly 208 may further include one or more members 210 for engaging a guide tube 400.

In one implementation, the distal end 204 of the deployment guide 200 includes the elongated tube 214 extending through a lumen on the guide shaft 206 and protruding from the distal tip 212 of the guide shaft 206. The elongated tube 214 includes a distal tip 228 adapted to guide the bone screw 600 into the hole 122 of the implant 100. In some implementations, the distal tip 228 includes one or more points, angles, contours, and/or the like. For example, as shown in FIGS. 18-20, the distal tip 228 may include a spike or wave feature formed by contours and points to anchor the deployment guide 200 into the surface of the joint to provide a stable anchor point during the deployment of the bone screw 600. Stated differently, the distal tip 228 is adapted to interface with surrounding and/or adjacent anatomical structures to provide additional support and guidance for the deployment guide 200. The window 220 may have a centerline that is coextensive with a centerline of the hole 122 to provide a deployment trajectory from the deployment guide 200 to the implant 100.

As can be understood from FIGS. 19A and 19B, in one implementation, the elongated tube 214 includes a guide passage 224 extending through a lumen of the elongated tube 214. The guide passage 224 includes an inner diameter adapted to permit passage of one or more delivery tools, for example, the bone screw 600 and/or the flexible shaft 506 of the bone screw driver 500. The window 220 provides an opening in the elongated tube 214 to the guide passage 224.

In one implementation, the distal end of the guide passage 224 includes one or more angled or contoured surfaces, which form the channel 222. The guide passage 224, the channel 222, and the window 220 form a deployment trajectory through the hole 122 of the implant 100. In one implementation, the channel 222 is oriented at an angle 226 between approximately 15° and 45° relative to the guide passage 224. The deployment trajectory, including the window 220, the angle 226 of the channel 222, and the inner diameter of the guide passage 224, is adapted to position an anchor, such as the bone screw 600, at a proper deployment orientation in the implant 100. As such, the deployment guide 200 is adapted to provide access to the implant 100 and to direct the bone screw driver 500 in delivering the bone screw 600 or other anchor at various orientations, based on the geometry of the deployment trajectory.

In some implementations, the guide tube 400 is inserted into the facet joint space, such that the anchoring forks 416 are positioned in the joint space. A delivery device, insertable into the lumen 412 of the guide tube 400, supports the implant 100 on a distal end of a tubular body. The implant 100 may be coupled to the distal end of the delivery device in a variety of manners. For example, the implant 100 may be threaded on, friction fit, clamped on, or the like. The delivery device coupled to the implant 100 is inserted through the lumen 412 of the guide tube 400 and implanted in the joint space, such that the implant 100 is position between the anchoring forks 416 in the joint space. The delivery device is decoupled from the implant 100, leaving the implant 100 in the joint space between the anchoring forks 416. The deployment guide 200, as shown in FIGS. 19A, 19B, and 20, is inserted into the guide tube 400 to deliver the bone screw 600. As described herein, the distal tip 228 interfaces with surrounding anatomical structures to provide additional support during the deployment of the bone screw 600. The bone screw driver 500 interfaced with the bone screw 600 is inserted into the guide passage 224 of the deployment device, which guides the bone screw along the deployment trajectory into the implant hole 122. The bone screw driver 500 is then decoupled from the bone screw 600 and the bone screw driver 500, the deployment guide 200, and the guide tube 400 are withdrawn, leaving the implant 100 anchored by the bone screw 600 in the joint space.

As shown in FIG. 20 the bone screw driver 500 moves the bone screw 600 along the guide passage 224 and the channel 222 towards the window 220. The bone screw driver 500 is inserted through the lumen of the guide shaft 206 of the deployment guide 200 and guided along the guide passage 224 of the elongated tube 214.

The collet 520 interfaces and retains the bone screw 600 in a non-co-axial direction as the bone screw driver 500 advances the bone screw 600 through the guide passage 224 of the elongated tube 214. As the tip 604 of the bone screw 600 approaches the window 220 of the elongated tube 214, the channel 222 causes the flexible shaft 506 of the bone screw collet drive 500 to bend along the contoured or angled surface in the distal end of the guide passage 224. The channel 222 and the window 220 guide the bone screw 600 along a deployment trajectory into the hole 122 of the implant 100. The angle 226 of the channel 222 orients the bone screw 600 relative to the hole 122 to facilitate the delivery of the bone screw 600 into the implant 100 using the bone screw driver 500.

It will be appreciated that the distal end of the deployment guide 200 may have a variety of different features adapted to orient the bone screw 600 relative to the hole 122 of the implant 100 to facilitate the delivery of the bone screw 600 or other anchor, such as one or more pins, curved members, screws, nails, barbed members, threaded members, and the like, into the implant 100 using the bone screw driver 500. Further, although a suture and collet system are described herein with respect to the bone screw driver 500, it will be understood that the bone screw driver 500 may have a variety of features adapted to deliver the bone screw 600 or other anchor along the deployment trajectory into the implant 100.

Figure 21:
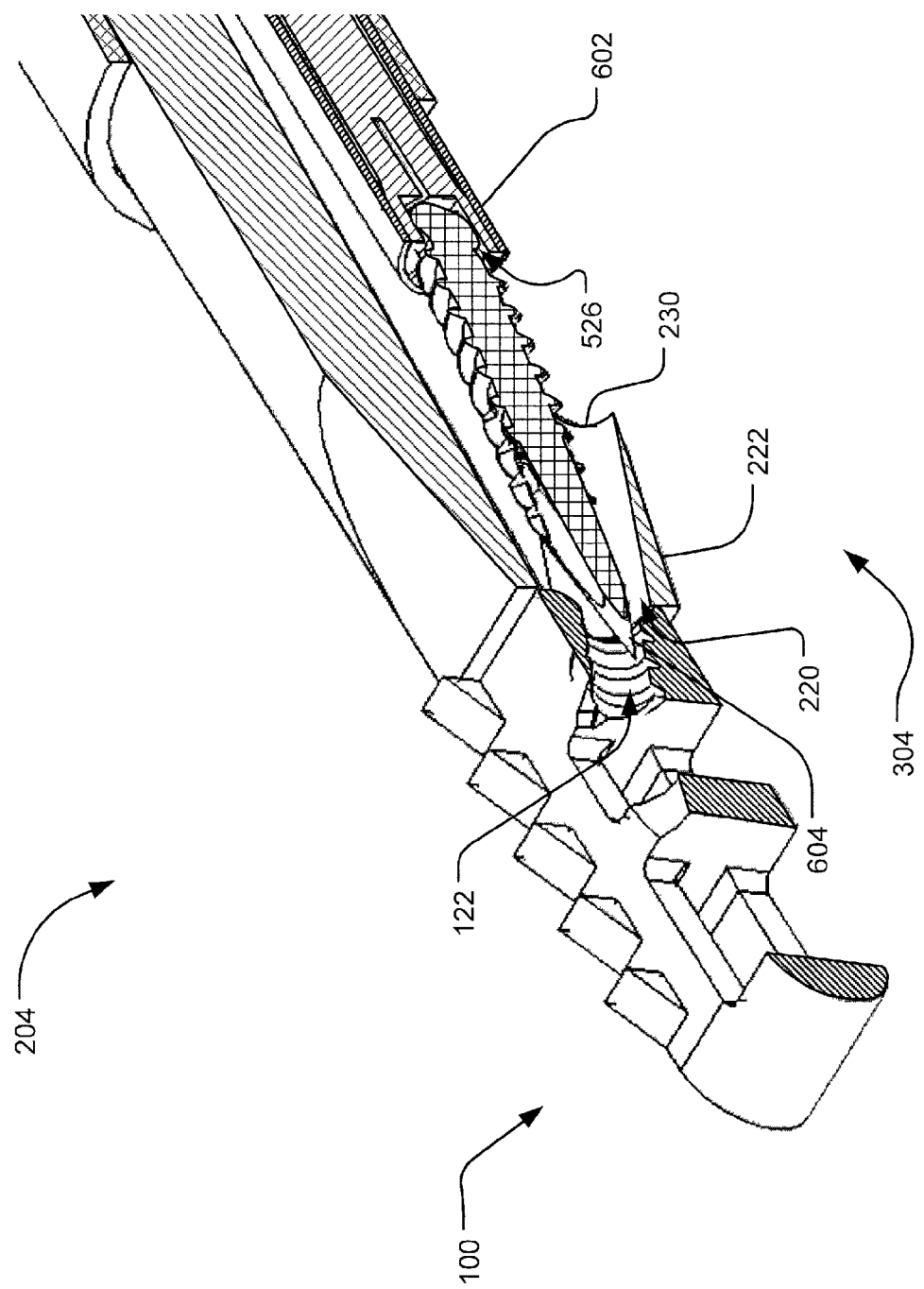
FIG. 21 is a perspective view of a longitudinal cross-section of a bone screw interfaced with the bone screw driver of FIG. 9 approaching an opening in an elongated tube of the distal end of the deployment guide of FIG. 2 along a channel into a threaded hole in the implant.

Referring to FIG. 21, which is a perspective view of a longitudinal cross-section of the bone screw 600 interfaced with the bone screw driver 500, the tip 604 of the bone screw 600 approaches the opening in the elongated tube 214 of the distal end 204 of the deployment guide 200 along the channel 222 into the hole 122 in the implant 100.

Figure 22:
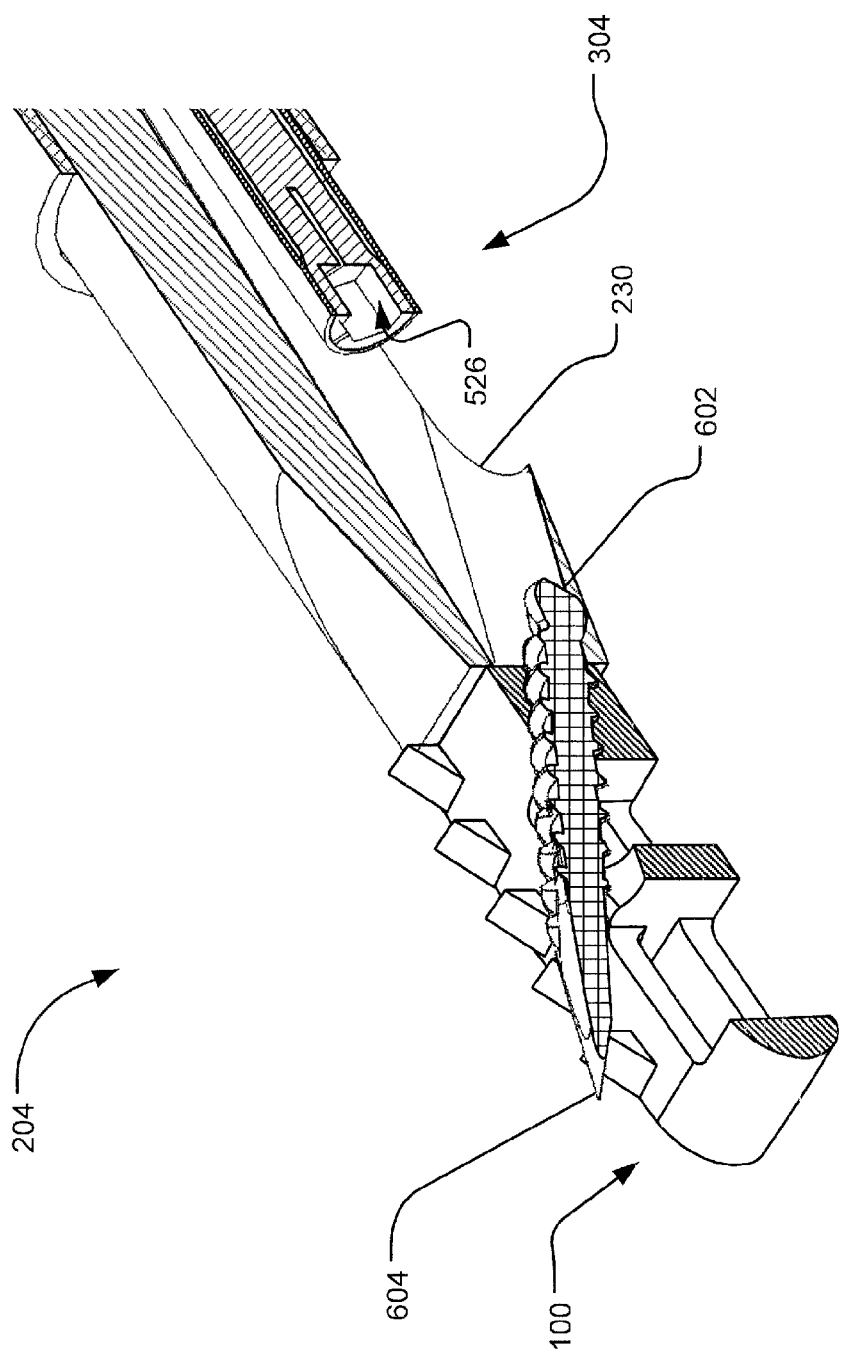
FIG. 22 shows the view of FIG. 21 with the bone screw delivered into the threaded hole of the implant and released from the collet.

Once the bone screw 600 is deployed into the hole 122 of the implant 100, as shown in FIG. 22, thereby anchoring the implant 100 in the joint, the collet 520 releases the bone screw head 602. The bone screw driver 500 is withdrawn from the deployment guide 200 along the guide passage 224.

Figure 23:
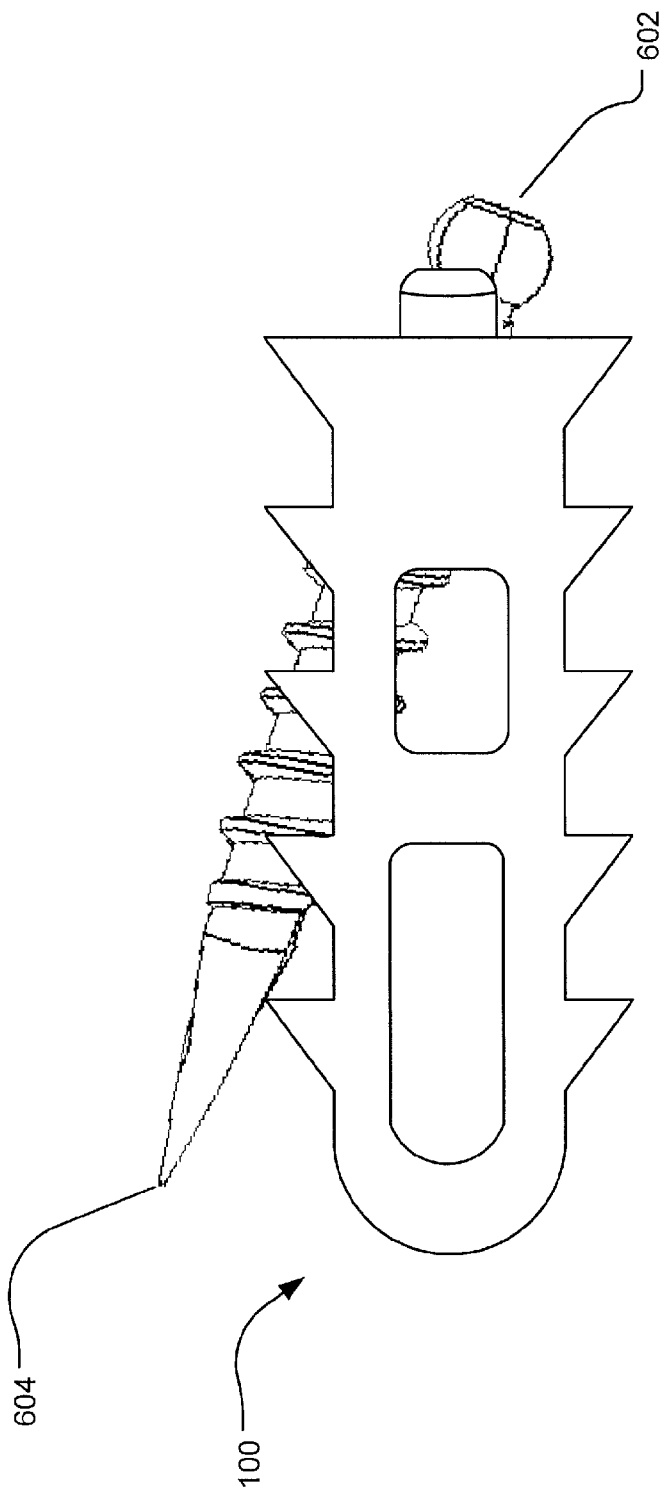
FIG. 23 displays a side view of the bone screw delivered into the implant.

The deployment guide 200 and the guide tube 400 are withdrawn from the percutaneous access site, leaving the bone screw 600 in the hole 122 of the implant 100, as shown in FIG. 23.

Figure 24:
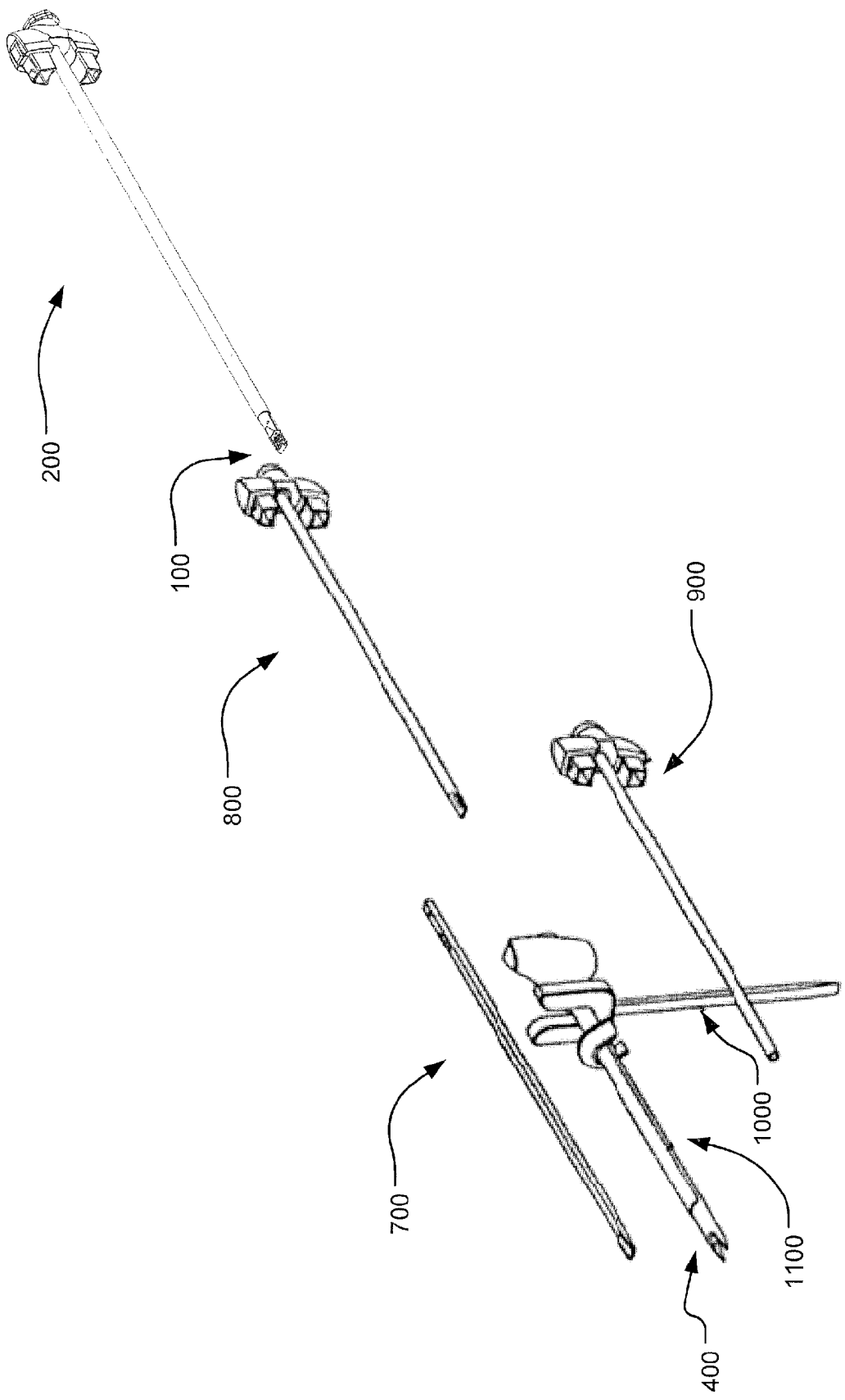
FIG. 24 shows various tools that may be included in a kit for implanting an implant.

FIG. 24 shows various tools that may be included in a kit for implanting the implant 100. In one implementation, the kit includes the deployment guide 200 interfaced with the implant 100 by the release driver 300, the guide tube 400, an access chisel 700, a chisel 800, an injector 900, a malleting tool 1000, and a decorticator 1100.

Generally, the access chisel 700 is routed through a percutaneous or minimally invasive incision under fluoroscopic guidance until the access chisel 700 extends out of the target facet joint. With the access chisel 700 so positioned, the decorticator 1100 can be grasped and distally routed over the access chisel 700, as shown in FIG. 24, such that the chisel shaft 702 is received in a lumen that extends longitudinally through the decorticator 1100. The decorticator 110 is removed after completion of decortication. The guide tube 400 is routed over the access chisel 700 until the anchor forks 416 are positioned in the facet joint space, and the access chisel 700 is withdrawn from the guide tube 400. The chisel 800 is then inserted through the guide tube 400 to decorticate the inferior and superior surfaces of the facet joint. In one implementation, with the guide tube 400 so positioned, the decorticator 1100 is routed over the guide tube 400, such that the decorticator 1100 abuts one or more lateral masses adjacent the target facet joint. In another implementation, the decorticator 1100 is routed over the access chisel 700 prior to insertion of the guide tube 400, such that the decorticator 1100 abuts one or more lateral masses adjacent the target facet joint. The decorticator 1100 decorticates the bone surfaces of the lateral masses. The decorticator 1100 is withdrawn and the deployment guide 200 is inserted into the guide tube 400 to implant the implant 100 into the facet joint between the forks 416 of the guide tube 400. The release driver 300 is released from the implant 100 and withdrawn from the deployment guide 200 and the bone screw driver 500 is inserted to into the deployment guide 200 to deliver the bone screw 600 into the hole 122 of the implant 100. The bone screw driver 500 and the deployment guide 200 are withdrawn, and the injector 900 is inserted into the guide tube 400 to insert bone paste into and around the facet joint occupied by the implant 100.

Turning to FIGS. 25A and 25B, in one implementation, the access chisel 700 includes a shaft 702 and a distal tip 704, which may include a tip the same or similar to the chisel 800. For example, the access chisel 700 can include a coped and/or chamferred tip. Additionally, the access chisel 700 can include ridges. Additionally, the access chisel 700 can include a radiopaque portion on the shaft 702 adapted to allow recognition of the location of the access chisel 700 while avoiding occlusion of the lateral view. The radiopaque portion can include a straight, round, square, or other shaped piece of material positioned near the distal end 704 of the access chisel 700 for locating the distal end 704.

In one implementation, a percutaneous or minimally invasive incision is made in the posterior region of the neck to lead to the target facet joint. The access chisel 700 is routed through the incision under fluoroscopic guidance until the distal tip 704 resides in the target facet joint and the chisel shaft 702 extends out of the patient via the incision. With the access chisel 700 so positioned, the decorticator 1100 can be grasped and distally routed over the access chisel 700, as shown in FIG. 24, such that the chisel shaft 702 is received in a lumen that extends longitudinally through the decorticator 1100.

Referring to back to FIG. 24, in one implementation, the malleting tool 1000 can include a longitudinally shaped shaft with a U-shaped decorticator interface at one end and a chamferred tip at the other end. The decorticator interface can be adapted for positioning around the guide tube 400 in a position just proximal to a malleting element of the decorticator 1100, as shown in FIG. 24. The U-shape of the decorticator interface may allow the malleting tool 1000 to be placed in position from the side of the guide tube 400 and selectively used as required to forcibly advance the decorticator 1100.

The chamferred end of the tool 1000 can be held in position while the user mallets near the decorticator interface end causing the interface to contact the malleting element on the decorticator 1100. The decorticator 1100 may then be retracted, rotated to a new radial position, advanced, and struck again for additional decortication. The malleting tool 1000 may rotate with the decorticator 1100 or it may remain in a position convenient for malleting. In addition to malleting, the malleting tool 1000 can be used to assist in separating several tools. That is, in some cases, the handles of a given tool piece can be difficult to separate from receiving portion. The chamferred tip can be used to wedge between a given handle and the receiving portion to assist in separating the devices.

Figure 26:
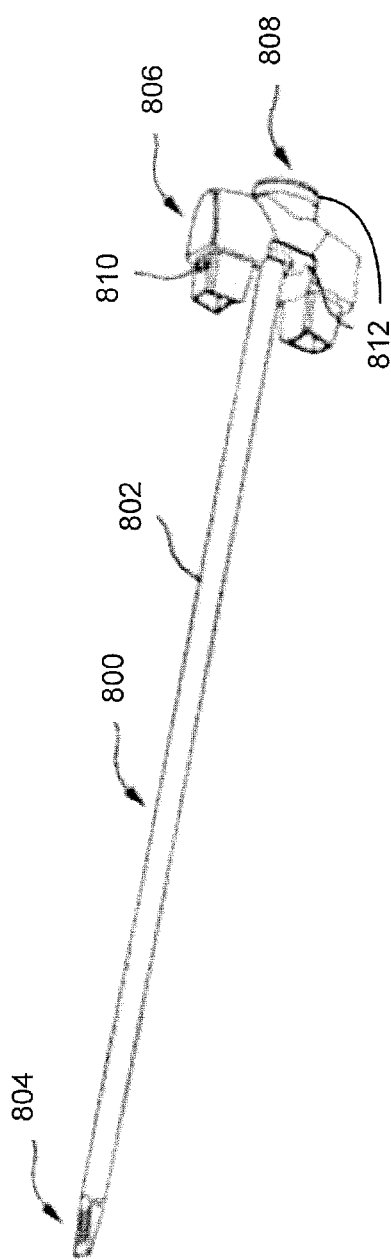
FIG. 26 shows a perspective view of an example chisel.

For a detailed discussion of the chisel 800, reference is made to FIG. 26. In one implementation, the chisel 800 includes a generally cylindrical cross-section forming a shaft 802, which may have a radius substantially equal to the inner radius of the tubular shaft portion 406 of the guide tube 400 allowing for slidable insertion of the chisel 800 within the guide tube 400. Alternatively, the radius of the shaft 802 may be smaller than the inner radius of the tubular shaft 406 providing for more play and adjustability of the chisel 800 and the guide tube 400 relative to one another. The chisel 800 may include a single or doubly chamferred tip 804 at a distal end or may have a coped distal end or a combination of coping and chamfering. The tip 804 may include a roughened surface on one or more sides to aid in anchoring or docking the chisel in the facet joint. Additionally, this roughened surface may allow for roughening or decorticating the inner surfaces of the facet joint. The tip 804 may have a length adapted to extend substantially across the facet joint.

The chisel 800 may further include a handle assembly 806 that includes a male member 810 positioned around the shaft 802, which may be sized and shaped to abut the female receiving portion 408 of the guide tube 400. The chisel 800 may also include a longitudinally extending lumen 808 and a malleting head 812.

Referring back to FIG. 24, in one implementation, the injector 900 includes a longitudinal delivery shaft adapted to fit within the guide tube 400. The longitudinal shaft may have an opening on its distal end for directing bone paste out the distal end of the shaft, allowing the paste to flow into and/or over the facet joint and/or outward toward the lateral mass of a facet joint. The injector 900 may be sleevably inserted into the guide tube 400 and advanced such that the distal end of the shaft is positioned between the forks 416.

Figure 27:
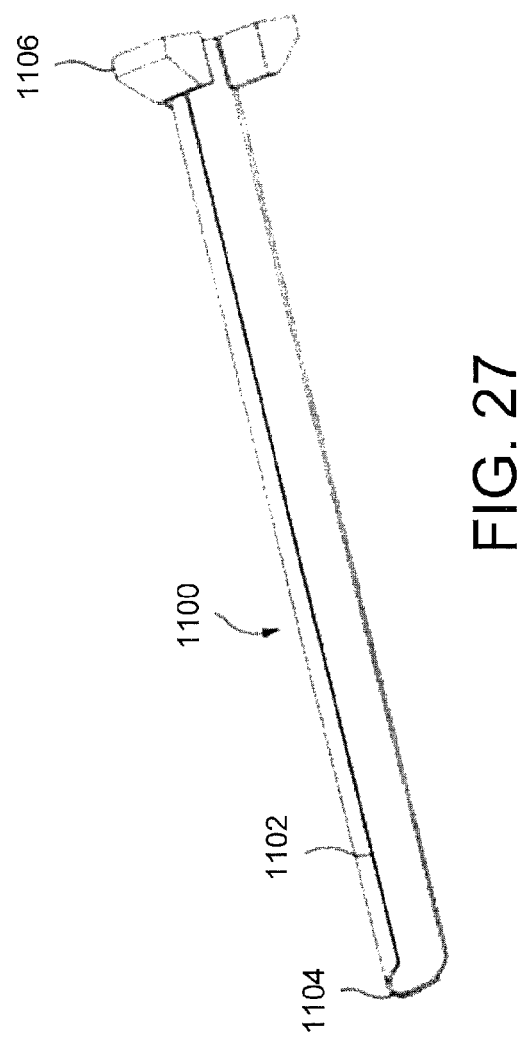
FIG. 27 displays an example decorticator.

For a detailed description of the decorticator 1100, reference is made to FIG. 27. In one implementation, the decorticator 1100 includes a tubular shaft portion 1102, an abrasive distal end 1104, and a handle 1106 at a proximal end. The tubular shaft 1102 may have an inner radius substantially equal to an outer radius of the tubular shaft 406 of the guide tube 400 and may allow for sliding movement of the decorticator 1100 along the length of the guide tube 400 and rotationally around the guide tube 400. In some implementations, the inner radius of the tubular shaft 1102 may be slightly or substantially larger than the outer radius of the tubular shaft 406 of the guide tube 400 allowing for more freedom of movement of the decorticator 1100.

The abrasive distal end 1104 of the decorticator 1100 may include serrated teeth as shown, or may include a more flat annular surface with a gritty surface. In the implementation shown in FIG. 27, the distal end 1104 of the tubular shaft portion 1102 is chamferred and the serrated teeth are located on the distal most end of the chamferred end allowing for a more directed and controllable decorticating process. As such, the decorticator 1100 shown is well suited for the intra facet process reflected by many of the implementations described herein. That is, the human anatomy of the cervical spine may be such that the lateral mass of the facet joints are not perpendicular to the surface of the facet joint.

Additionally, to properly place the forks 416 of the guide tube 400 within the joint, the guide tube 400 may be positioned substantially parallel to articular surfaces of the facet joint. As such, the guide tube 400 may not be positioned perpendicular to the lateral masses of the facet joints and may actually be directed with a downward slope as it extends in the distal direction. Where the decorticator 1100 has an non-chamferred annular end, depending on anatomy, the decorticator 1100 may be able to be placed in contact with the superior lateral mass, but may be unable to reach or contact the inferior lateral mass. In one implementation, the chamferred end of the tubular shaft portion 1102 will allow the distal tip 1104 of the chamferred end to reach and decorticate the inferior lateral mass. This chamferred distal end 1104 may define an angle to the longitudinal axis. Additionally, the teeth may be relatively large or they may relatively small and may extend along the full perimeter surface of the chamferred end rather being positioned solely at the tip of the chamferred end 1104. Additionally, a beveled edge may run along the periphery of the chamferred end 1104. That is, along the ovular shape created by the chamferred tubular shaft portion 1102, the edge is beveled. As such, when the guide tube 400 is inserted into the patient and/or when the decorticator 1100 is advanced along the guide tube 400, the beveled edge may assist in avoiding tissue snags, and the decorticator 400 may be placed in contact with the lateral mass of the facet joints in a much smoother process and may avoid damage to neighboring tissues.

The handle 1106 of the decorticator 1100 may include a gripping surface along its peripheral edge and may sleevably receive the tubular shaft portion 1102. The handle 1106 may also include radially extending bores (not shown) adapted to receive a gripping tool to provide for better control and a higher amount of torsional leverage when decorticating the lateral masses of the facet joint or to allow for malleting in the longitudinal direction of the decorticator 1100 to cause forceful decortication of the lateral mass. The decorticator 1100 may then be retracted, rotated to a new radial position, advanced, and struck again for additional decortication.

For more detail regarding the tools 700-1100, see U.S. patent application Ser. No. 12/653,283, which was filed Dec. 10, 2009 and entitled "Verbal Joint Implants and Delivery Tools." This application is incorporated by reference in its entirety herein.

Figure 28:
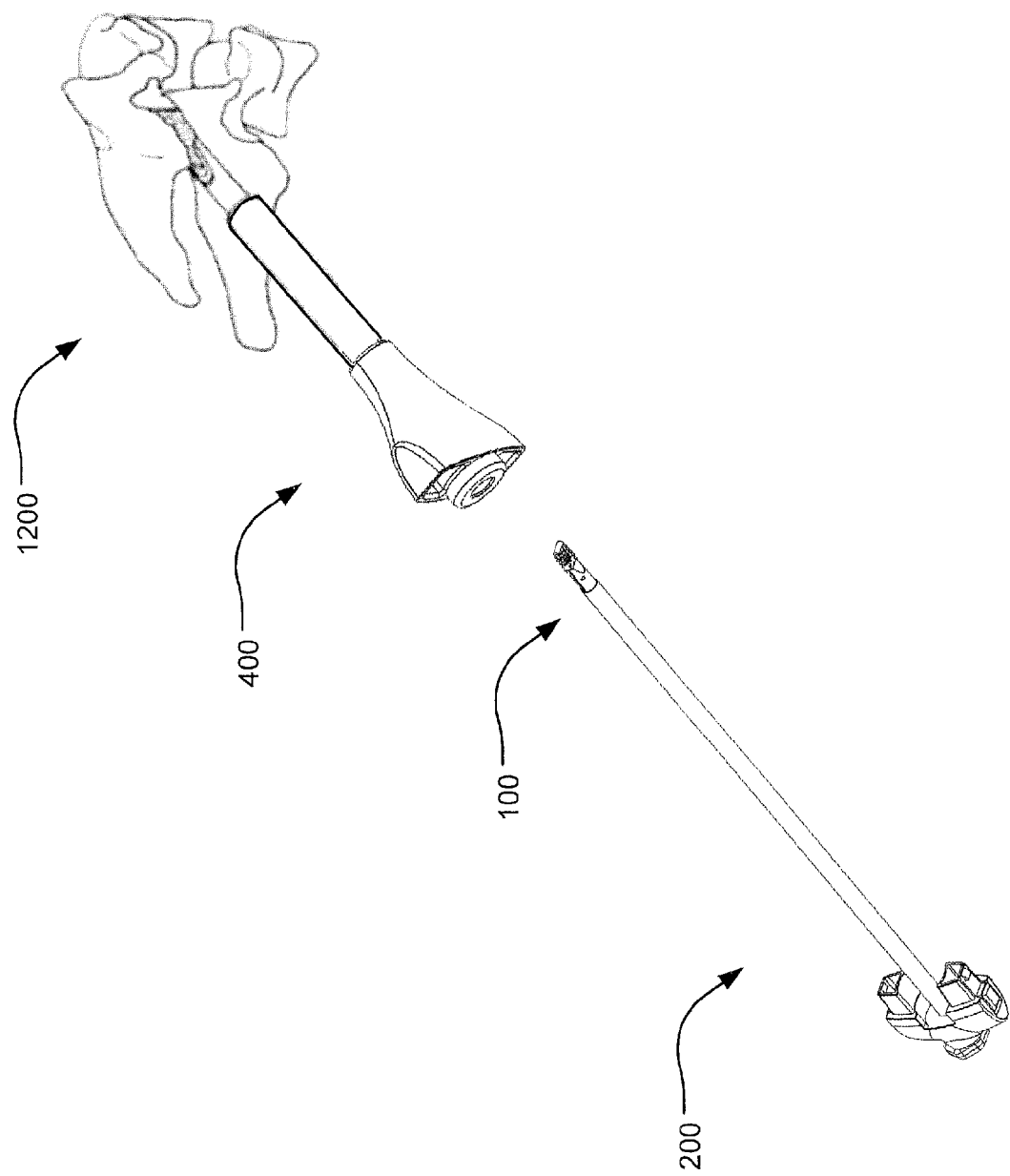
FIG. 28 shows the insertion of the deployment device of FIG. 6 into the guide tube of FIG. 8 to implant an implant into the facet joint.

FIG. 28 shows the insertion of the deployment device 200 of FIG. 6 into the guide tube 400 of FIG. 8 to implant the implant 100 into the facet joint 1200, as described herein. FIGS. 29A and 29B show the implant 100 during and after insertion into the facet joint 1200, respectively.

Figure 30:
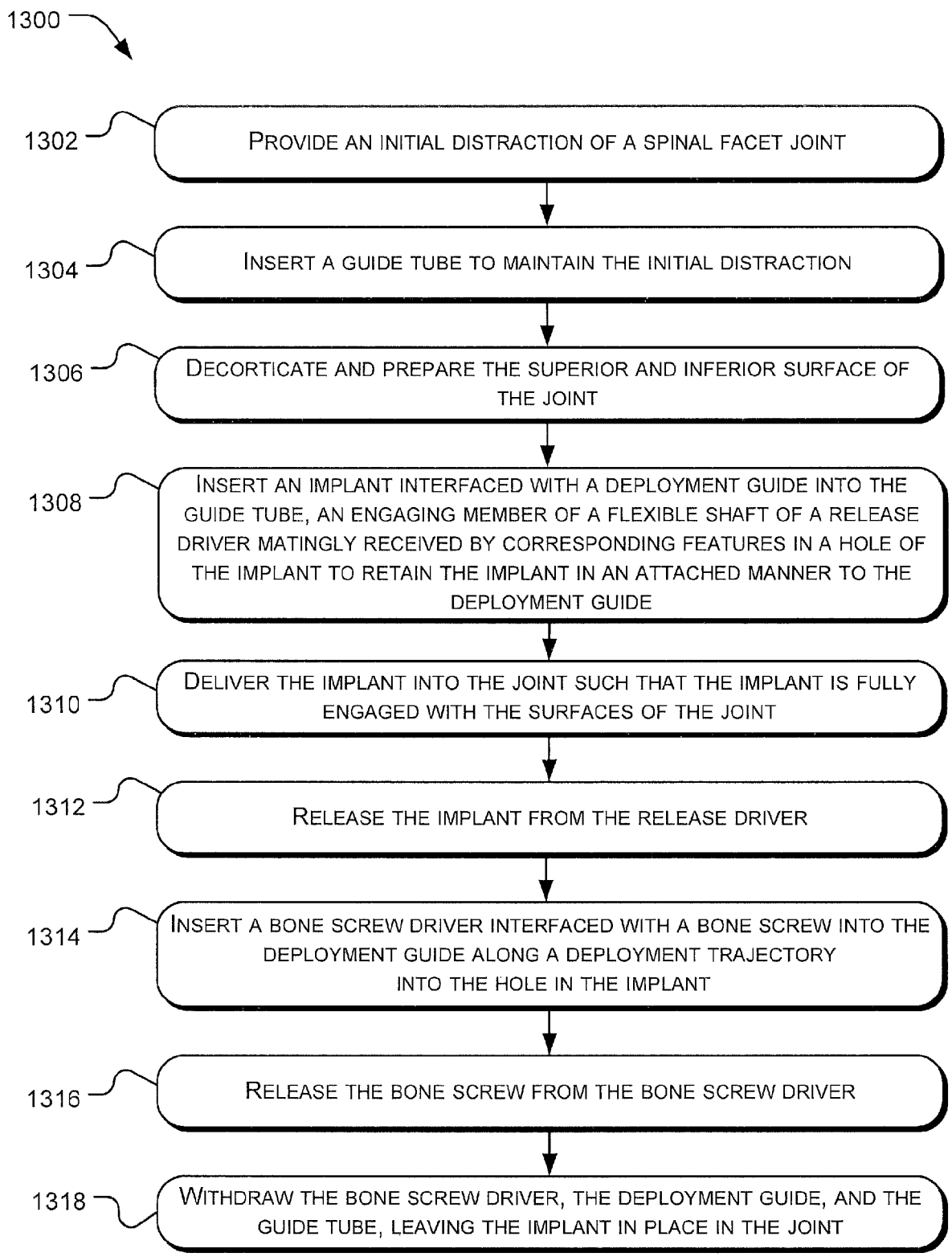
FIG. 30 illustrates example operations for implanting an implant in a spinal facet joint space and for deploying a bone screw to anchor the implant.

FIG. 30 illustrates example operations 1300 for implanting an implant in a spinal facet joint space and for deploying a bone screw to anchor the implant.

In one implementation, a providing operation 1302 provides an initial distraction of the spinal facet joint 1200. For example, the providing operation 1302 may include inserting, under fluoroscopy and via a minimally invasive posterior incision, the access chisel 700 into the spinal facet joint between vertebral bodies of the spine to provide for initial distraction of the spinal facet joint 1200. The providing operation 1302 may further include confirming a depth and placement of the access chisel 700 using radiolucent markers or holes in a shaft of the access chisel 700. An inserting operation 1304 inserts the guide tube 400 to maintain the initial distraction. In one implementation, the inserting operation 1304 inserts the guide tube 400 over the access chisel 700 to maintain the initial distraction and the access chisel 700 is removed.

A decorticating operation 1306 decorticates and prepares the superior and inferior surface of the spinal facet joint. For example, in one implementation, the decorticating operation 1306 includes inserting a decorticating chisel 800 into the guide tube 400; decorticating and preparing the surfaces of the joint 1200 with distal surfaces of the decorticating chisel 800; and removing the decorticating chisel 800 from the guide tube 400. Further decortication may occur on the lateral masses of the facet joint via a tubular or semi-tubular decorticator 1100 that may be routed over the access chisel 700 prior to the guide tube 400 deployment or over the exterior of the guide tube 400 in the case of the semi-tubular decorticator 1100.

An inserting operation 1308 inserts the deployment guide 200 interfaced with the implant 100 into the guide tube 400, as shown in FIG. 28. In one implementation, the implant 100 is interfaced with or otherwise attached to a distal end of an elongated tube extending from a lumen of a shaft of the deployment guide 200. To retain the implant 100 in an attached manner to the deployment guide 200, the release driver 300 is fully inserted through a guide passage extending through a lumen of the elongated tube, and an engaging member of a flexible shaft of the release driver 300 engages the implant 100 through a window providing an opening in the elongated tube to the guide passage. A hole in the implant 100 having corresponding features matingly receives the engaging member of the flexible shaft of the release driver 300. A channel, formed from a contoured or angled surface in the distal end of the guide passage, causes the flexible shaft of the release driver to bend, such that the implant 100 is retained in tension. The window is disposed at the distal end of the guide passage relative to the channel.

A delivering operation 1310 delivers the implant 100 into the spinal facet joint 1200. In some implementations, the delivering operation 1310 includes malleting using the malleting tool 1000 to fully engage the implant 100 with the joint 1200. The implant 100 may have teeth or other engaging features to engage surfaces of the joint 1200. Once the delivering operation 1310 delivers the implant into the spinal facet joint 1200, such that the implant 100 is fully engaged with the surfaces of the spinal facet joint 1200 to maintain the initial distraction, a releasing operation 1312 releases the implant 100 from the release driver 300. In one implementation, the releasing operation 1312, disengages the engaging member of the flexible shaft from the implant 100. The releasing operation 1312 withdraws the release driver 300 from the deployment guide 200, leaving the implant 100 in the joint 1200 with the implant 100 between the prongs of the guide tube 400, the prongs being still located in the joint space 1200, and the distal end of the deployment guide 200 abutting against the proximal surface of the implant 100, as shown in FIG. 16.

In one implementation, to anchor the implant 100 in the joint 1200, an inserting operation 1314 delivers a bone screw 600 or similar anchor into the hole of the implant 100 by inserting a bone screw driver 500 interfaced with the bone screw 600 into the deployment guide 200 along a deployment trajectory. The bone screw driver 500 may include a collet interfaced with the bone screw 600. Stated differently, a head of the bone screw 600 is retained in a socket of the collet by retracting the collet proximally into a retaining ring of a flexible shaft at a distal end of the bone screw driver 500, thereby tightening the socket to retain the bone screw head. The collet retains the bone screw 600 regardless of the axial alignment. As the bone screw 600 approaches the window of the elongated tube, the channel causes the flexible shaft of the bone screw driver 500 to bend along the contoured or angled surface in the distal end of the guide passage. The channel and the window guide the bone screw 600 along the deployment trajectory into the hole of the implant 100. Once the bone screw 600 is deployed into the implant 100, thereby anchoring the implant 100 in the joint 1200, as shown in FIG. 29B, a releasing operation 1318 releases the bone screw head, and a withdrawing operation 1318 withdraws the bone screw driver 500, the deployment guide 200, and the guide tube 400, thereby leaving the implant 100 anchored by the bone screw 600 in place in the spinal facet joint 1200.

The description above includes example systems, methods, techniques, instruction sequences, and/or computer program products that embody techniques of the present disclosure. However, it is understood that the described disclosure may be practiced without these specific details.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A deployment guide system comprising: an implant comprising:
    a top surface and a proximal end including an opening, wherein at least a portion of the opening extends through the implant at an angle relative to the top surface such that when a bone anchor is used, the bone anchor extends through the opening; and
    a deployment guide comprising:
        a guide shaft having a lumen extending between a proximal end and a distal end;
        an elongated tube extending through at least a portion of the guide shaft lumen and protruding from a distal tip of the guide shaft;
        a guide passage extending through a lumen of the elongated tube;
        a channel formed from one or more surfaces at a distal end of the guide passage, the channel being oriented at an angle relative to the guide passage;
        a window disposed at a distal end of the channel, the window providing an opening in the elongated tube to the guide passage, the channel and the guide passage forming a deployment trajectory through the window,
    wherein the elongated tube interfaces with the proximal end of the implant, such that the window is oriented relative to the opening in the implant.

2. The deployment guide system of claim 1, wherein the implant is a cervical facet joint implant.

3. The deployment guide system of claim 1, wherein the orientation of the implant opening relative to the window places the implant opening relative to the deployment trajectory to facilitate deployment from the guide passage to the implant opening.

4. The deployment guide system of claim 1, wherein the guide passage has an inner diameter sized to permit passage of the bone anchor interfaced with a bone anchor driver along the deployment trajectory.

5. The deployment guide system of claim 4, wherein the bone anchor driver includes a flexible shaft, the channel adapted to cause the flexible shaft to bend along the deployment trajectory as the bone anchor approaches the window.

6. The deployment guide system of claim 1, wherein the guide passage has an inner diameter sized to permit passage of a release driver along the deployment trajectory, the release driver having an engagement member adapted to engage the implant opening to retain the implant in an attached manner to the elongated tube.

7. The deployment guide system of claim 6, wherein the release driver includes a flexible shaft, the channel adapted to cause the flexible shaft to bend to retain the implant in tension.

8. The deployment guide system of claim 1, wherein the angle the channel is oriented at relative to the guide passage is between approximately 15° and 45°.

9. The deployment guide system of claim 1, wherein the one or more surfaces forming the channel are contoured or angled.

10. The deployment guide system of claim 1, wherein the elongated tube is adapted to interface with the proximal end of the implant sized for insertion into at least one of: a cervical facet space; thoracic facet space; lumbar facet space; cervical disc space; thoracic disc space; or lumbar disc space.

11. The deployment guide system of claim 1, wherein the elongated tube includes a distal surface adapted to interface with a proximal surface of the implant, the window defined in the distal surface.

12. The deployment guide system of claim 1, wherein the elongated tube includes a distal tip forming the window, the distal tip adapted to engage anatomical surfaces to provide stability.

13. The deployment guide system of claim 4, further comprising the bone anchor and bone anchor driver, wherein the bone anchor driver comprises:
    a flexible shaft extending from a proximal end to a distal end, the flexible shaft adapted to bend along a deployment trajectory;

a collet including a distal surface having a socket defined therein, the socket being adapted to receive and retain a head of the bone anchor; and a handle assembly at the proximal end of the flexible shaft, the handle assembly adapted to move the collet relative to a retaining ring of the flexible shaft between an engaged position and a released position, the engaged position tightening the socket and the released position loosening the socket.

14. The deployment guide system of claim 1, wherein the bone anchor is a bone screw.

15. The deployment guide system of claim 13, wherein the engaged position retains the bone anchor in a non-coaxial direction.

16. The deployment guide system of claim 13, wherein the collet protrudes from the retaining ring in the released position.

17. The deployment guide system of claim 13, wherein the collet is retracted into the flexible shaft in the engaged position.

18. A bone anchor deployment system comprising:

a bone anchor; and a bone anchor deployment device comprising:

a flexible shaft extending from a proximal end to a distal end, the flexible shaft adapted to bend along a deployment trajectory;

a socket at the distal end of the flexible shaft retains the bone anchor in a non-coaxial position;

a guide shaft having a lumen and a distal tip;

an elongated tube extending through at least a portion of the guide shaft lumen and protruding from the distal tip of the guide shaft;

a guide passage extending through a lumen of the elongated tube;

a channel formed from one or more surfaces at a distal end of the guide passage, the channel being oriented at an angle relative to the guide passage, the channel adapted to cause the shaft to bend; and a window disposed at a distal end of the channel, the window providing an opening in the elongated tube to the guide passage, the channel and the guide passage forming the deployment trajectory through the window.

19. The bone anchor deployment system of claim 18, wherein the angle the channel is oriented at relative to the guide passage is between approximately 15° and 45°.

20. The bone anchor deployment system of claim 18, wherein the retention of the bone anchor in a non-coaxial direction permits the bone anchor to be deployed between approximately 0° and 45° of axial variation.

* * * * *